US010226577B2

(12) United States Patent
Radmer et al.

(10) Patent No.: US 10,226,577 B2
(45) Date of Patent: Mar. 12, 2019

(54) DRUG DELIVERY DEVICE WITH TIME INDICATOR FEATURE

(71) Applicant: Novo Nordisk A/S, Bagsvaerd (DK)

(72) Inventors: Bo Radmer, Hilleroed (DK); Andre Larsen, Dragor (DK); Mikkel Avlund, Soeborg (DK); Morten Revsgaard Frederiksen, Copenhagen K (DK)

(73) Assignee: Novo Nordisk A/S, Bagsvaerd (DK)

( * ) Notice: Subject to any disclaimer, the term of this patent is extended or adjusted under 35 U.S.C. 154(b) by 85 days.

(21) Appl. No.: 15/035,040

(22) PCT Filed: Nov. 13, 2014

(86) PCT No.: PCT/EP2014/074475
§ 371 (c)(1),
(2) Date: May 6, 2016

(87) PCT Pub. No.: WO2015/071354
PCT Pub. Date: May 21, 2015

(65) Prior Publication Data
US 2016/0263327 A1 Sep. 15, 2016

Related U.S. Application Data

(60) Provisional application No. 61/906,979, filed on Nov. 21, 2013.

(30) Foreign Application Priority Data

Nov. 13, 2013 (EP) ..................... 13192790
May 20, 2014 (EP) ..................... 14169056

(51) Int. Cl.
A61M 5/31 (2006.01)
A61M 5/20 (2006.01)
(Continued)

(52) U.S. Cl.
CPC ............... A61M 5/31 (2013.01); A61M 5/20 (2013.01); A61M 5/3158 (2013.01);
(Continued)

(58) Field of Classification Search
CPC ...... A61M 2005/3126; A61M 2205/52; A61M 2207/00; A61M 5/20; A61M 5/24;
(Continued)

(56) References Cited

U.S. PATENT DOCUMENTS 9,457,142 B2 10/2016 Day et al.
2012/0080029 A1* 4/2012 Koerner .............. A61M 15/009
128/203.12

FOREIGN PATENT DOCUMENTS

JP 2013512060 A 4/2013
WO 9524233 A1 9/1995
(Continued)

Primary Examiner — Brandy S Lee
(74) Attorney, Agent, or Firm — Wesley Nicolas

(57) ABSTRACT

A drug delivery device is provided comprising a housing having an exterior surface, a drug-filled reservoir with an outlet, drug expelling means, and a flexible sheet. On the flexible sheet is formed or mounted input means adapted to be actuated corresponding to an event indicative of drug being expelled, a display adapted to display a time parameter, a processor, and an energy source. The processor is adapted to, based on input from the detection means, control the display to display a time parameter related to the time the event was detected, and the flexible sheet is attached at least in part to the outer surface of the housing.

14 Claims, 27 Drawing Sheets

(51) Int. Cl.
    *G04G 9/00*         (2006.01)
    *G06F 19/00*       (2018.01)
    *A61M 5/24*        (2006.01)
    *A61M 5/315*       (2006.01)

(52) U.S. Cl.
CPC .... *A61M 5/31536* (2013.01); *A61M 5/31551* (2013.01); *A61M 5/31568* (2013.01); *G04G 9/00* (2013.01); *G06F 19/00* (2013.01); *G06F 19/3456* (2013.01); *G06F 19/3468* (2013.01); *A61M 5/24* (2013.01); *A61M 5/31553* (2013.01); *A61M 5/31583* (2013.01); *A61M 2005/3126* (2013.01); *A61M 2205/52* (2013.01); *A61M 2207/00* (2013.01)

(58) Field of Classification Search
CPC ................ A61M 5/31; A61M 5/31536; A61M 5/31551; A61M 5/31553; A61M 5/31568; A61M 5/3158; A61M 5/31583; G04G 9/00; G06F 19/3456; G06F 19/00
See application file for complete search history.

(56) References Cited

FOREIGN PATENT DOCUMENTS

| | | | | |
|---|---|---|---|---|
| WO | 9730742 | | 8/1997 | |
| WO | WO 9730742 | * | 8/1997 | ............ A61M 5/178 |
| WO | 99/43283 | | 9/1999 | |
| WO | 2010/023303 | | 3/2010 | |
| WO | 2013004844 A1 | | 1/2013 | |

* cited by examiner

Fig. 15.1
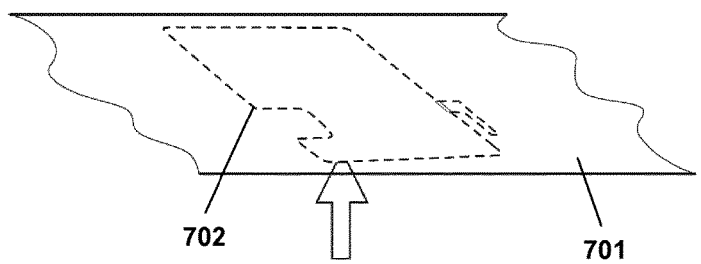
Fig. 15.2
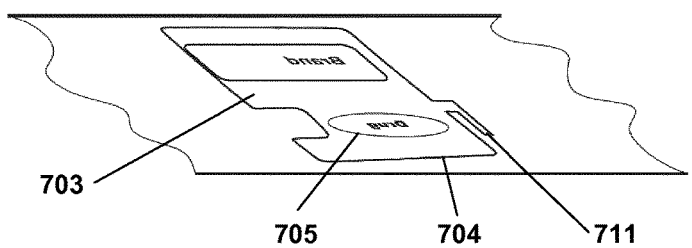
Fig. 15.3
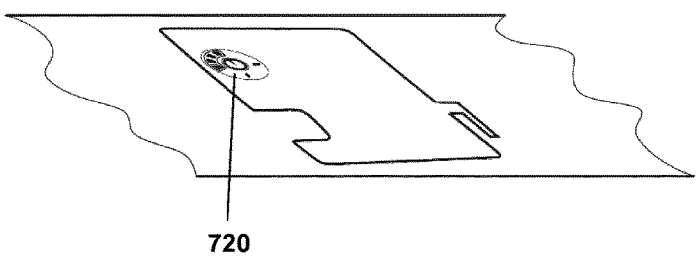
Fig. 15.4
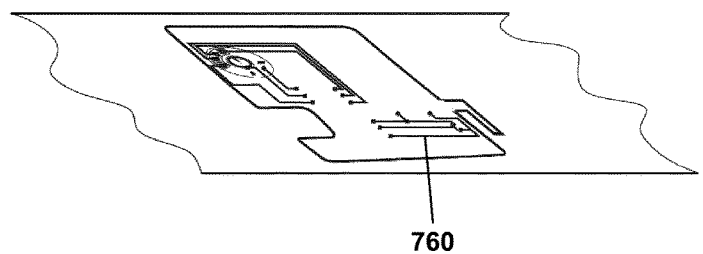

Fig. 15.5
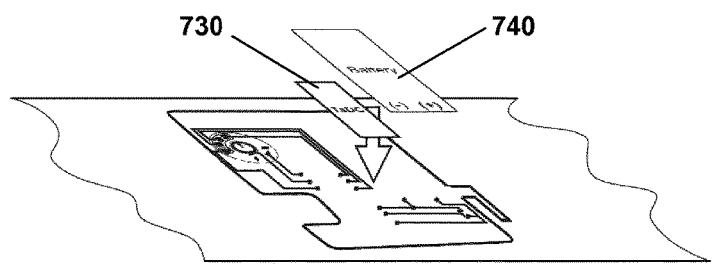
Fig. 15.6
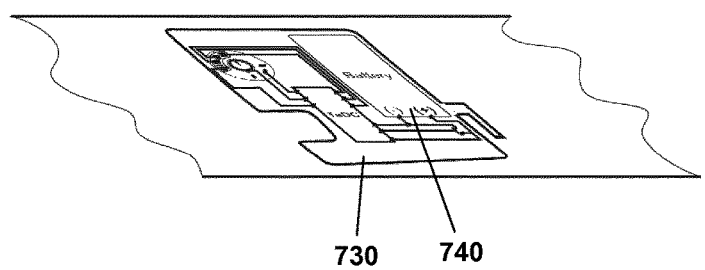
Fig. 15.7
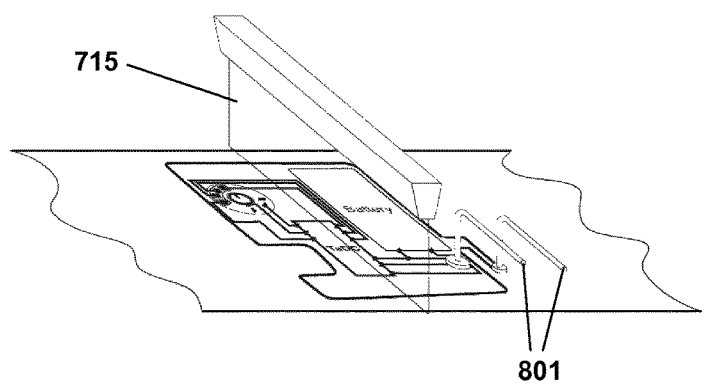
Fig. 15.8
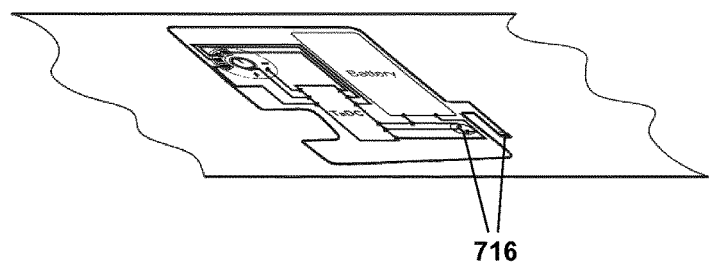

Fig. 15.9
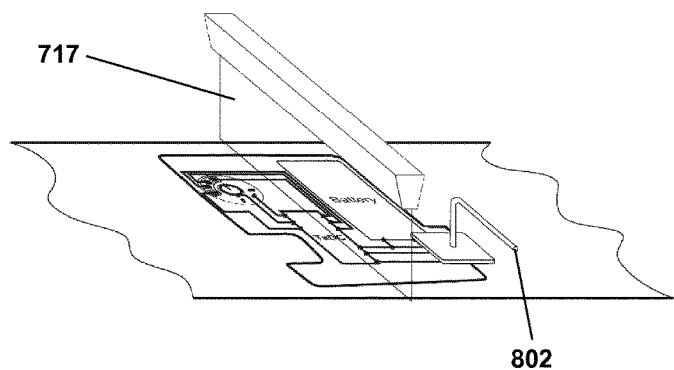
Fig. 15.10
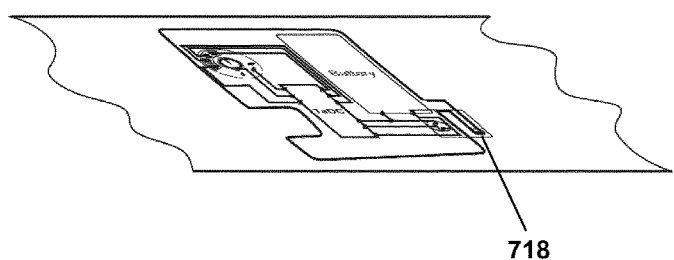
Fig. 15.11
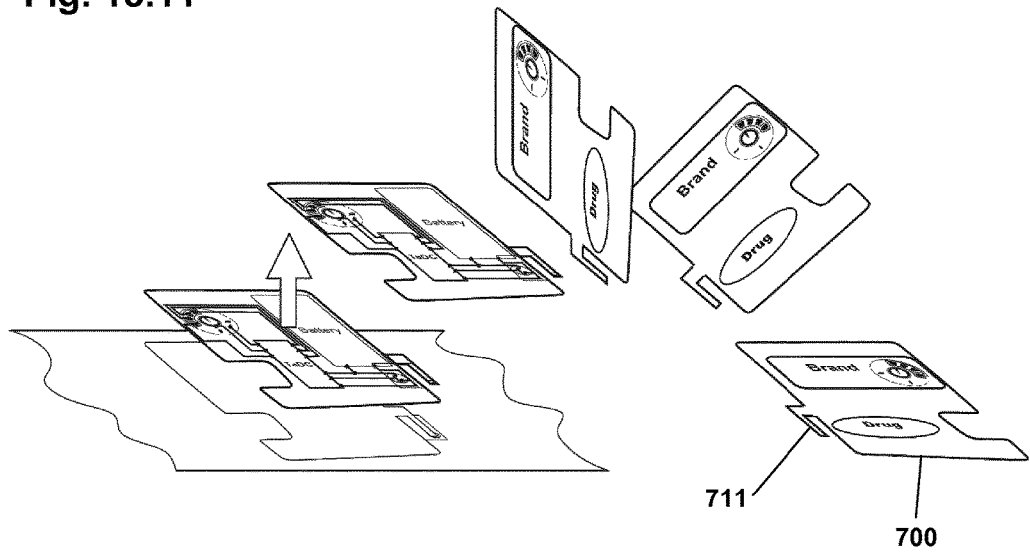

Fig. 15.12
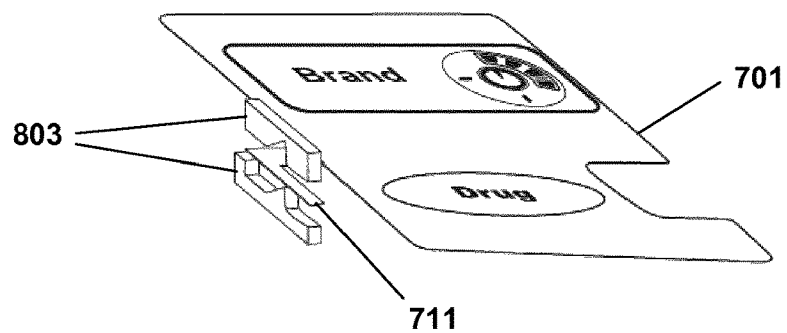
Fig. 15.13
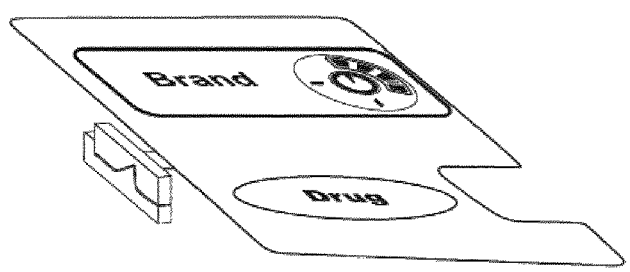
Fig. 15.14
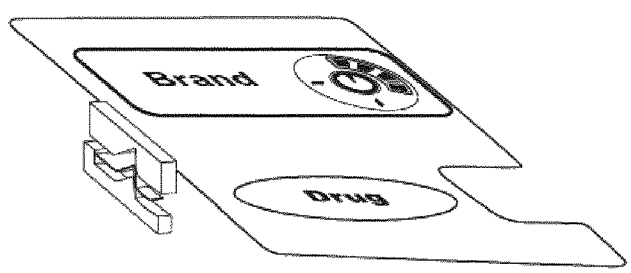
Fig. 15.15
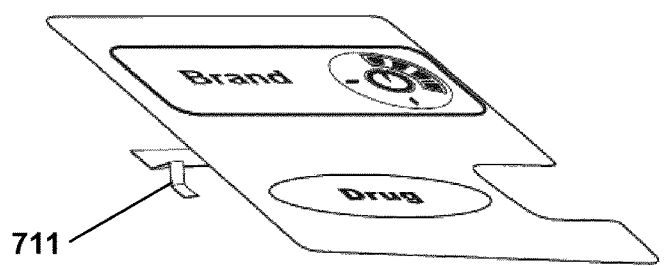

Fig. 15.16
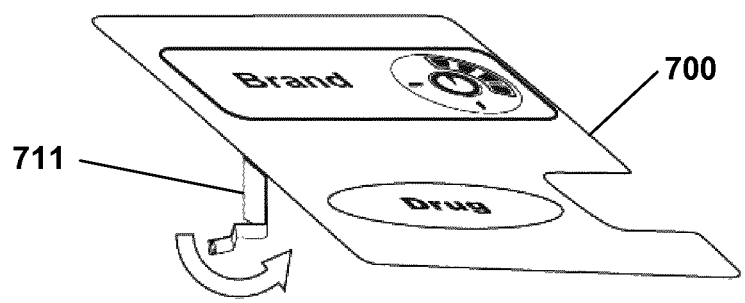
Fig. 15.17
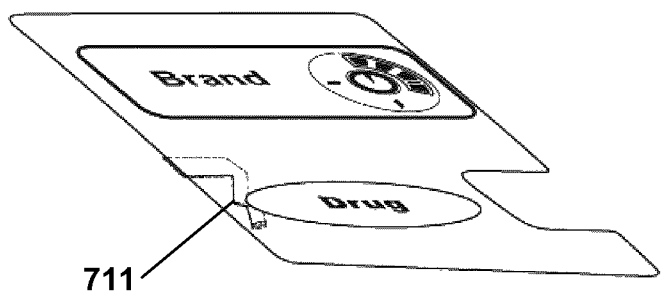

Fig. 15.18
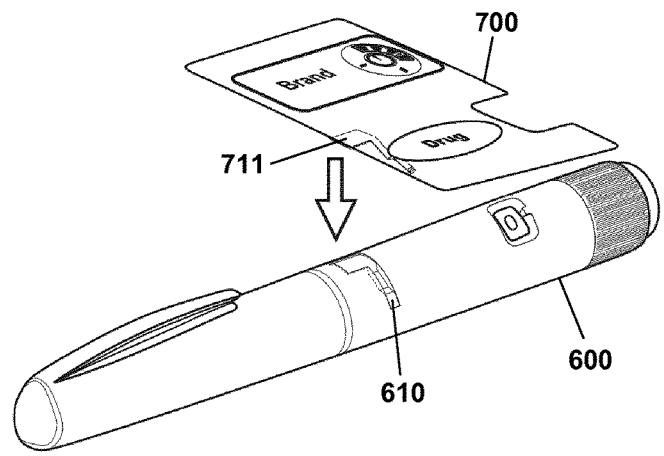
Fig. 15.19
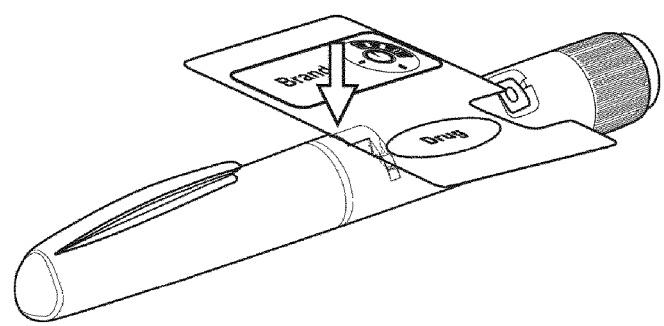
Fig. 15.20
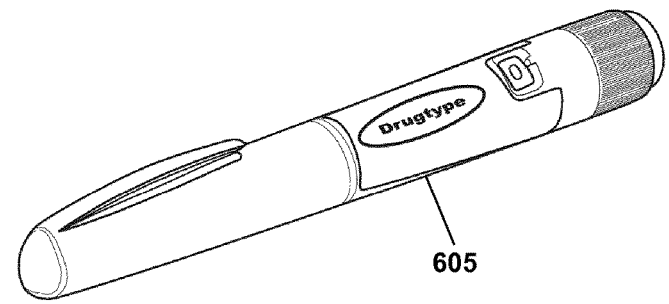
Fig. 15.21
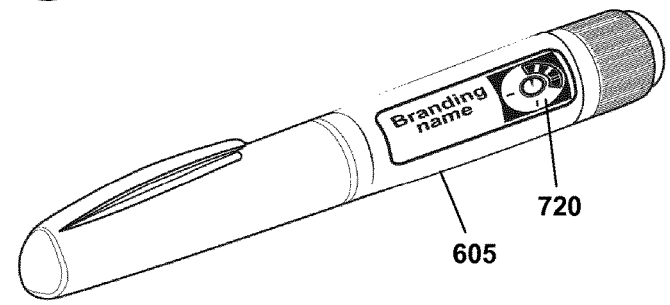

Fig. 16.1
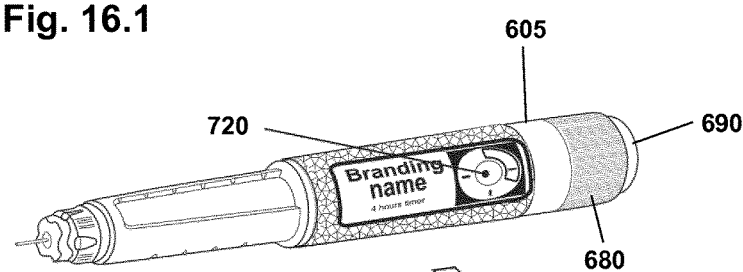
Fig. 16.2
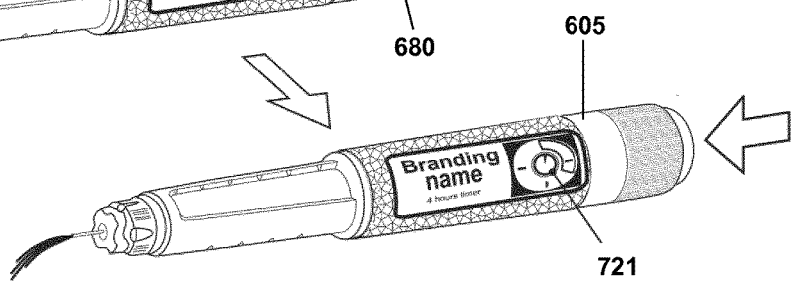
Fig. 16.3
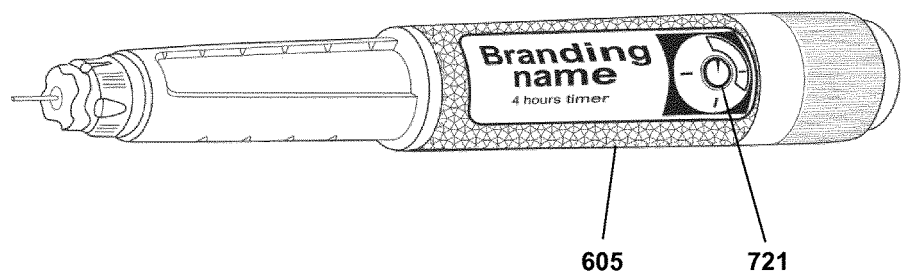

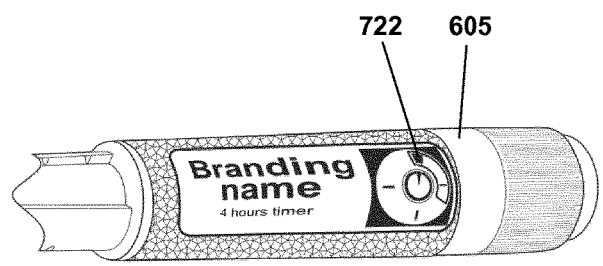
Fig. 16.4
Fig. 16.5
Fig. 16.6
Fig. 16.7
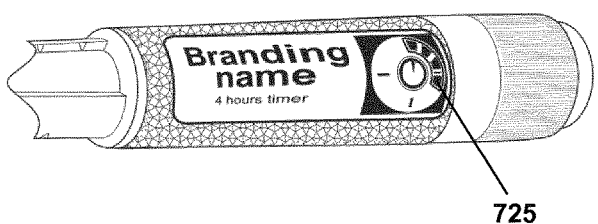

Fig. 26
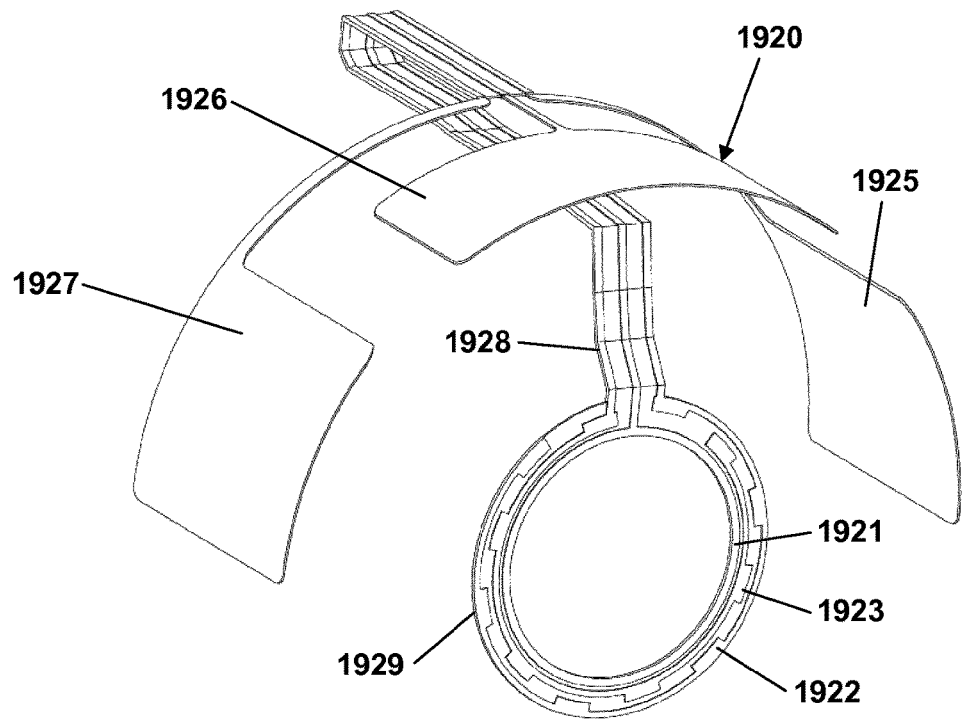
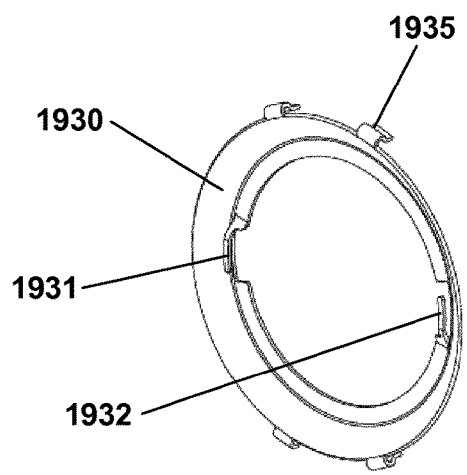

Fig. 28.1
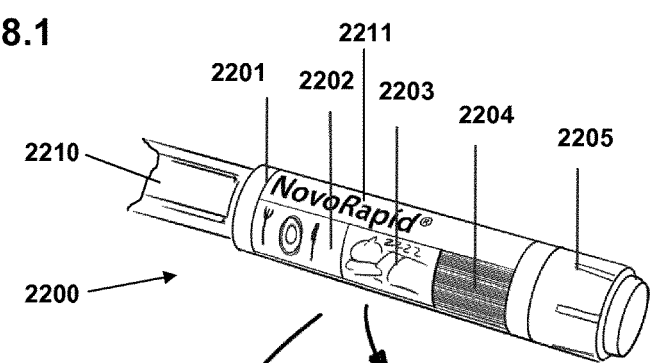
Fig. 28.3
Fig. 28.2
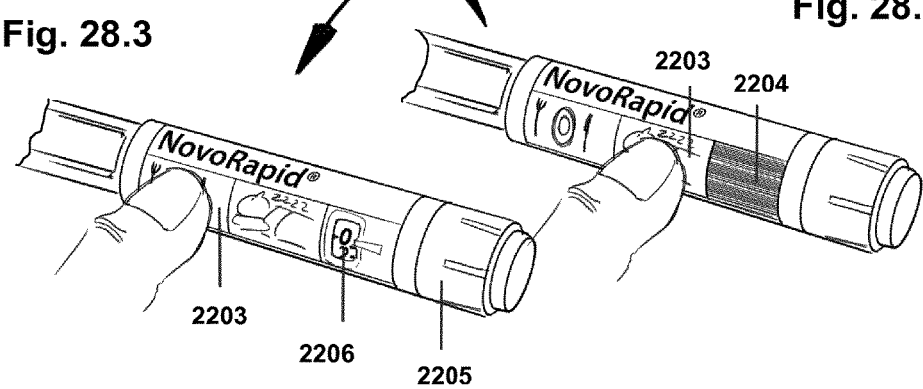

DRUG DELIVERY DEVICE WITH TIME INDICATOR FEATURE

CROSS-REFERENCE TO RELATED APPLICATIONS

This application is a 35 U.S.C. § 371 National Stage application of International Application PCT/EP2014/074475 (published as WO 2015/071354), filed Nov. 13, 2014, which claims priority to European Patent Application 13192790.7, filed Nov. 13, 2013, and European Patent Application 14169056.0, filed May 20, 2014; this application claims priority under 35 U.S.C. § 119 to U.S. Provisional Application 61/906,979; filed Nov. 21, 2013.

The present invention generally relates to medical devices comprising indicator means configured to display information relating to an expelled dose of drug. In a specific aspect the displayed information relates to the time a given dose of drug was expelled.

BACKGROUND OF THE INVENTION

In the disclosure of the present invention reference is mostly made to drug delivery devices comprising a threaded piston rod, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

The typical diabetes patient will require injections of insulin several times during the course of a week or a day. For other types of drug the intervals between drug deliveries may be shorter or longer. However, typical injection devices do not address the problem of a user not remembering when the last injection was administered.

Even shortly after administering a dose of insulin, the user now and then will be in doubt as to whether he actually carried out an injection or not. This could be after minutes or even hours after the intended time for performing an administration. Thus, there exist the potential hazard that the patient chooses not to take his or her medication or that it is taken twice.

Some prior art devices, such as the electronic drug delivery device disclosed in WO 97/30742, are provided with an electronic monitoring system adapted to automatically start an electronic timer when a selected dose is expelled and to show the progress in time on an electronic display. Such an injection device generally provides a satisfactorily solution to the problem addressed above. However, for simpler devices such as disposable drug delivery devices, i.e. so-called pre-filled devices, the incorporation of this kind of electronics would normally not be economically viable. In addition, such a solution may not be environmentally acceptable due to the potential increase in the disposal of electronic components.

Addressing this issue, WO 99/43283 discloses a timer device which is intended to be used with pre-filled injection pens, where the timer device is configured for releasable attachment to the pre-filled pen so that the timer device can be removed from a pen once it is ready for disposal and be attached to a new pen. The timer device is configured to detect when an injection is performed and to communicate this via indicator lights that remains turned on for a certain time period from the administration of the dose.

As an alternative to using an add-on device which has to be removed and attached each time the user has emptied a pre-filled drug delivery device, WO 2010/023303 discloses a drug delivery device provided with a non-electronic time delay indicator integrated in the proximal push button, the arrangement providing a simple and cost-effective solution allowing the indicator to be provided as an integral part of a pre-filled device. The time delay indicator may be configured to be in a first visual state prior to activation of the actuator, to be in a second visual state responsive to activation of the actuator, and to be in a third visual state after lapse of a pre-defined time interval measured from the activation of the actuator. The second visual state may be defined as a distinct visual appearance throughout the lapse of the pre-defined time interval or, alternatively, define a gradually changing visual indication. This second visual state should in either case be directly distinguishable by the operator of the device from the first and third visual states.

Having regard to the above, it is an object of the present invention to provide a time indicator device for a drug delivery device which cost-effectively can be incorporated in a pre-filled and thus disposable device, yet provides the "authority", precision and safety of use associated with a traditional electronic device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device is provided, comprising a housing having an exterior surface, a drug-filled cartridge or means for receiving a drug-filled cartridge, and drug expelling means. The cartridge comprises an outlet and an axially displaceable piston. The drug expelling means comprises a drive member adapted to engage and axially move the piston to thereby expel an amount of drug from the cartridge through the outlet, and an indicator member arranged to move corresponding to an action performed on or by the drug delivery device. The drug delivery device further comprises a flexible sheet on which is formed or mounted input means adapted to be actuated, directly or indirectly, by movement of the indicator member, a display adapted to display a time parameter, a processor, and an energy source, the flexible sheet being mounted at least in part to the exterior of the housing. The input means may be in the form of galvanic contacts and/or contact-less based on e.g. induction. The processor is adapted to, based on input from the input means, control the display to display a time parameter related to the time the input means was actuated.

By the above arrangements a very simple and inexpensive electronic system is provided on a drug delivery device, the low cost allowing it to be formed integrally with a pre-filled disposable drug delivery device. Indeed, the electronic system could also be incorporated in a durable device.

The input means may be in the form of a switch structure adapted to be actuated between a first and a second state. The switch structure may e.g. comprise a number of stationary contact areas formed or mounted on a contact area of the flexible sheet, the drug delivery device further comprising a moveable switch structure adapted to engage the stationary contact areas to thereby actuate the input means, the moveable switch structure being adapted to be moved by the indicator member. The moveable switch structure may be formed integrally with the flexible sheet, the moveable switch structure comprising a contact area, wherein the contact area is arranged in its operational position by bending of the flexible sheet. In the present context the term "bending" should be understood broadly including e.g. folding, turning, rotating.

Alternatively the drug delivery device may comprise one or more switch members arranged corresponding to an opening formed in the housing, at least one switch member being a moveable switch member projecting into the opening and being adapted to be moved by the indicator member, whereby the one or more switch members form a switch assembly adapted to be actuated between a first and a second state. The switch assembly may be preassembled or formed from switch members mounted individually. The flexible sheet is mounted to cover the opening and comprises contact means (terminals) adapted to engage corresponding terminals on the switch assembly to thereby provide the input means.

In an exemplary embodiment the indicator member is adapted to rotate from a set position corresponding to a set dose amount and to an end-of-dose position in which the set dose has been expelled, the input means being actuated when the indicator member has reached the end-of-dose position. During rotation of the indicator member the input means may be actuated more than once. The processor is adapted to control the display to display (i) a time parameter indicating the time when the input means was actuated, e.g. using the HH:MM format, or (ii) a time parameter indicating the time since input means was actuated, e.g. a dynamic timer using the HH:MM format or a simple version using segments for e.g. each hour.

The indicator member may have a first axial position when the drug expelling means is in a dose setting state, and a second axial position when the drug expelling means is in an expelling state, the input means being adapted to be actuated by the indicator member with the indicator member only in the second axial position.

In a further exemplary embodiment the indicator member is adapted to move from an initial position to a set position when a dose is being set, the input means being actuated when the indicator member is moved away from the initial position. As above, the processor is adapted to control the display to display a time parameter indicating the time when input means was actuated, or a time parameter indicating the time since input means was actuated.

In a yet further exemplary embodiment, one or more flexible members provided with contact means may be bonded to the flexible sheet to provide a composite switch structure. Depending on the design and the assembly process for the drug delivery device as well as the switch design a composite switch structure may be the most cost-effective. For example, a switch structure may be mounted inside or outside the device during assembly, the flexible sheet being mounted on an external surface of the device such that contact is established between the two structures. The input means may comprise more than one switch, the switches being of the same or different designs.

In a yet further exemplary embodiment the amount of rotation of the indicator means corresponds to the amount of drug expelled from a reservoir by the expelling means, the input means being adapted to be actuated corresponding to the amount of rotation of the indicator means. The processor is adapted to (i) based on input from the input means calculate the amount of drug expelled corresponding to the amount of rotation, and (ii) control the display to display the calculated amount. In addition time information related to the calculated drug amount may be display. The processor is adapted to create a dose log comprising dose amounts and associated time values.

Alternatively the amount of rotation of the indicator means corresponds to a user-set amount of drug to be expelled from a reservoir by the expelling means, the input means being adapted to be actuated corresponding to the amount of rotation of the indicator means, and the processor is adapted to (i) based on input from the input means calculate the set amount of drug to be expelled corresponding to the amount of rotation, and (ii) control the display to display the calculated amount. For such a design it would be possible to use the electronic display instead of a mechanical display, e.g. as on a traditional dose drum, this allowing e.g. larger numerals to be used.

The indicator member used to detect a dose amount may be the same as described above for detecting an event or it may be a different member. Alternatively the electronic label may be adapted to only detect and display dose amounts.

The housing may have a curved exterior portion, and the flexible sheet and the display may be mounted at least in part to the curved exterior and/or interior portion of the housing. For example, the drug delivery device may have a pen configuration with a general round or oval form, the flexible sheet being applied to the housing as an exterior "label", e.g. by adhesive. Depending on the design of the input means the housing may be designed with openings allowing the input means to be actuated by internal mechanical elements, or portions of the flexible sheets comprising input means may be threaded through such openings and attached to an interior surface of the housing. Further input means may be arranged in the interior of the drug delivery device and adapted to cooperate with input means of the flexible sheet.

To cost-effectively provide a "label-like" electronic assembly one or more or all of the detection means, display, processor, and energy source may be in the form of printed electronics. An antenna may be also formed on the flexible sheet by printing, the processor being adapted to transmit data to an external receiver via the antenna.

In a further aspect of the invention a flexible sheet with electronics as described above is provided, the sheet being adapted to be mounted on a drug delivery of the type described above.

In a further aspect of the invention a method of a method of assembling a drug delivery device is provided. The method comprises the step of providing a fully or partly assembled drug delivery device, switch means, and a flexible sheet. The fully or partly assembled drug delivery device comprises a housing with an exterior surface and an opening, as well as drug expelling means arranged in the interior of the housing and comprising an indicator member arranged to move corresponding to an action performed on or by the drug delivery device. The switch means is adapted to be mounted at least partly in the opening and be actuated by the indicator member, the switch means comprising contact terminals. On the flexible sheet is formed or mounted input terminals, a display adapted to display a time parameter, a processor adapted to, based on input from the input terminals, control the display to display a time parameter related to the time the input was detected, and an energy source. The method comprises the further steps of mounting the switch means to the housing corresponding to the opening, and mounting the flexible sheet to the housing exterior surface with the input terminals operational connected to the switch means contact terminals, the flexible sheet covering the opening. By such an assembly design it would be possible to skip mounting of the switch means and mount a traditional label covering the opening in the housing, this allowing for efficient and cost-effective manufacturing of pen variants with or without an electronic label.

In a yet further aspect of the invention a drug delivery device is provided, comprising a drug-filled cartridge comprising a first type of drug, drug expelling means for expelling an amount of drug from the cartridge, a first visual indicator (e.g. label) indicating the first type of drug (e.g. fast-acting insulin), a first user input means (e.g. active button) associated with a second visual indicator (e.g. showing a meal) indicating the first type of drug, a second user input means (e.g. a "dummy" button) associated with a third visual indicator (e.g. showing a bed) indicating a second type of drug, and blocking means having a first state preventing normal operation of the drug expelling means, and a second state allowing normal operation of the drug expelling means. In such an arrangement actuation of the first user input means brings the blocking means from the first state to the second state, thereby allowing normal operation of the drug expelling means, and actuation of the second user input means does not bring the blocking means from the first state to the second state, thereby preventing normal operation of the drug expelling means.

As appears, the above-described arrangement helps assure that a user takes the correct intended type of drug, e.g. type of insulin, as the user has to confirm the type of drug to be taken. The concept is thus not to merely have the user confirm a choice, e.g. like "do you want to inject a dose of drug X—yes or no?", but providing the user with a "positive" incorrect option.

The drug expelling means may comprise dose setting means allowing a user to set a desired dose amount of drug to be expelled, and display means for displaying the size of a dose being set, wherein the blocking means in the first state prevents the set dose to be viewed and in the second state allows the set dose to be viewed. The display means may be in the form of printed digits shown in a display opening, the blocking means in the first state preventing the digits to be viewed through the window, and in the second state allowing the digits to be viewed through the window. The blocking means may be in the form of a window fully or partly covering the opening and having a first non-transparent state and a second transparent state.

In a further aspect of the invention a corresponding method of using a drug delivery device is provided, comprising the steps of (i) providing a drug delivery device comprising a first type of drug, the device being adapted to be operated between a first state in which the device is not fully operatable, and a second state in which the device is fully operational, the device comprising first user confirm means corresponding to the first type of drug and adapted to bring the device from the first to the second state when operated, and second user confirm means corresponding to a second type of drug and having no influence on the device state when actuated, (ii) operating the first user confirm means to confirm that the user desires to administer a dose of the first type of drug, and (iii) operating the device to administer a dose of the first type of drug.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Other specific drugs could be growth hormone and drugs for the treatment of haemophilia and inflammation.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof.

BRIEF DESCRIPTION OF THE DRAWINGS

In the following the invention will be further described with reference to the drawings, wherein FIG. 26 shows a further alternative for a switch design for a pen with external electronics.

In the figures like structures are mainly identified by like reference numerals.

DESCRIPTION OF EXEMPLARY EMBODIMENTS

Figure 1A:
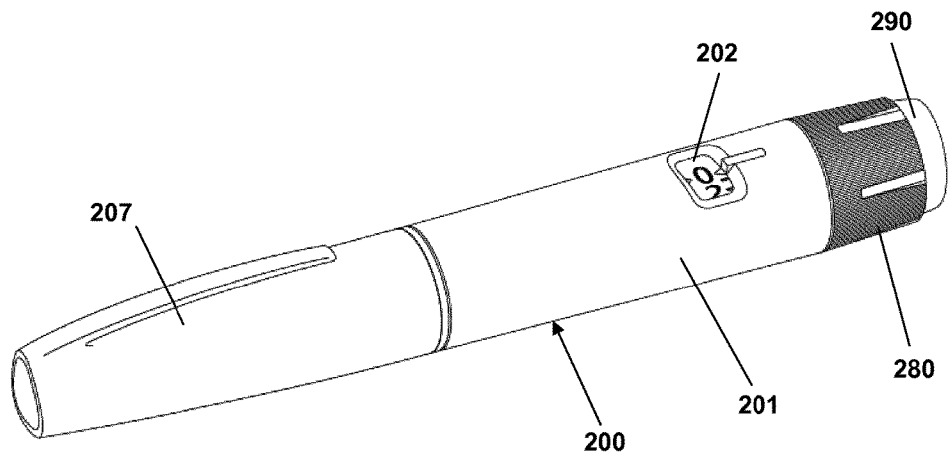
FIG. 1A shows a pen device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessary can be assembled to provide a unitary or functional assembly during a given assembly procedure but is merely used to describe components grouped together as being functionally more closely related.

Before turning to embodiments of the present invention per se, an example of a pre-filled drug delivery will be described, such a device providing the basis for the exemplary embodiments of the present invention. Although the pen-formed drug delivery device 200 shown in FIG. 1 may represent a "generic" drug delivery device, the actually shown device is a Flex-Touch® pre-filled drug delivery pen as manufactured and sold by Novo Nordisk A/S, Bagsværd, Denmark.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a non-removable cartridge holder attached to the proximal portion, the cartridge holder having openings allowing a portion of the cartridge to be inspected as well as distal coupling means 215 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 280 serves to manually set a desired dose of drug shown in display window 202 and which can then be expelled when the button 290 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
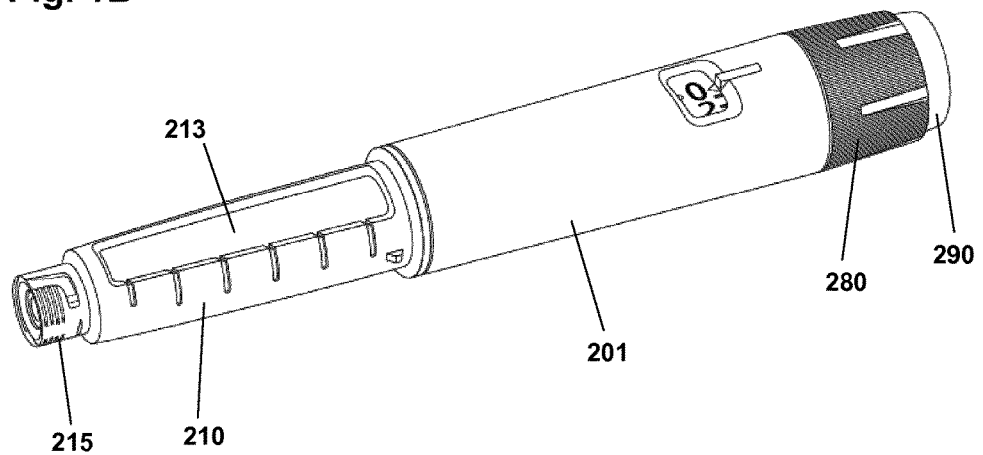
FIG. 1B shows the pen device of FIG. 1A with the pen cap removed.

Although FIG. 1 shows a drug delivery device of the pre-filled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the invention relates to electronic circuitry adapted to be incorporated in and interact with a drug delivery device, an exemplary embodiment of such a device will be described for better understanding of the invention.

Figure 2:
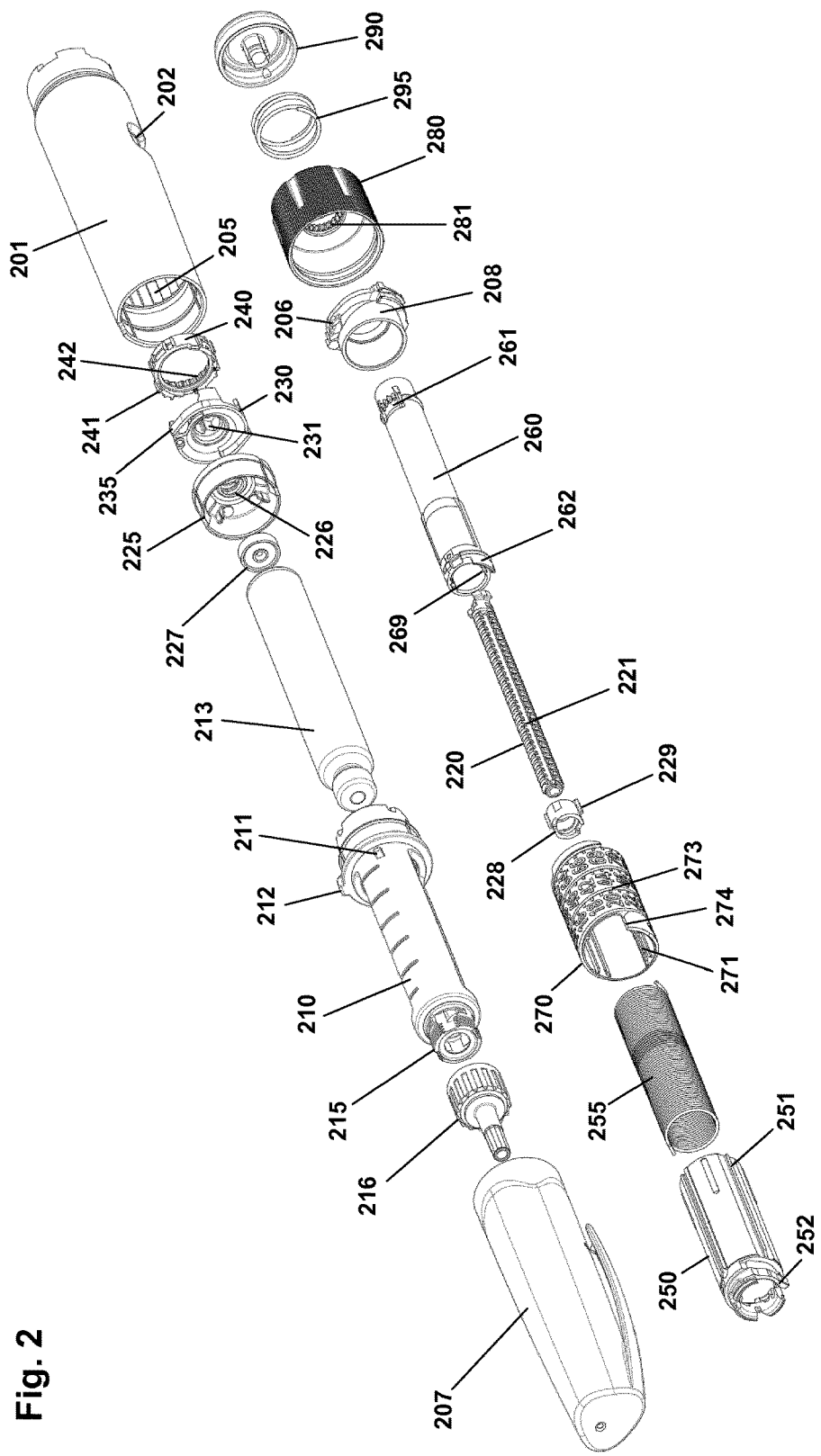
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 200 shown in FIG. 1. More specifically, the pen comprises a tubular housing 201 with a window opening 202 and onto which a cartridge holder 210 is fixedly mounted, a drug-filled cartridge 213 being arranged in the cartridge holder. The cartridge holder is provided with distal coupling means 215 allowing a needle assembly 216 to be releasable mounted, proximal coupling means in the form of two opposed protrusions 211 allowing a cap 207 to be releasable mounted covering the cartridge holder and a mounted needle assembly, as well as a protrusion 212 preventing the pen from rolling on e.g. a table top. In the housing distal end a nut element 225 is fixedly mounted, the nut element comprising a central threaded bore 226, and in the housing proximal end a spring base member 208 with a central opening is fixedly mounted. A drive system comprises a threaded piston rod 220 having two opposed longitudinal grooves and being received in the nut element threaded bore, a ring-formed piston rod drive element 230 rotationally arranged in the housing, and a ring-formed clutch element 240 which is in rotational engagement with the drive element (see below), the engagement allowing axial movement of the clutch element. The clutch element is provided with outer spline elements 241 adapted to engage corresponding splines 204 (see FIG. 4B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 231 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 235 adapted to engage corresponding ratchet teeth 205 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 4A and 4B.

On the piston rod an end-of-content (EOC) member 228 is threadedly mounted and on the distal end a washer 227 is rotationally mounted. The EOC member comprises a pair of opposed radial projections 229 for engagement with the reset tube (see below).

The dial system comprises a ratchet tube 250, a reset tube 260, a scale drum 270 with an outer helically arranged row of dose numerals, a user-operated dial member 280 for setting a dose of drug to be expelled, a release button 290 and a torque spring 255 (see FIG. 3). The reset tube is mounted axially locked inside the ratchet tube but is allowed to rotate a few degrees (see below). The reset tube comprises on its inner surface two opposed longitudinal grooves 269 adapted to engage the radial projections 229 of the EOC member, whereby the EOC can be rotated by the reset tube but is allowed to move axially. The clutch element is mounted axially locked on the outer distal end portion of the ratchet tube 250, this providing that the ratchet tube can be moved axially in and out of rotational engagement with the housing via the clutch element. The dial member 280 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 290 is axially locked to the reset tube but is free to rotate. A return spring 295 provides a proximally directed force on the button and the thereto mounted reset tube. The scale drum 270 is arranged in the circumferential space between the ratchet tube and the housing, the drum being rotationally locked to the ratchet tube via cooperating longitudinal splines 251, 271 and being in rotational threaded engagement with the inner surface of the housing via cooperating thread structures 203, 273, whereby the row of numerals passes the window opening 202 in the housing when the drum is rotated relative to the housing by the ratchet tube. The torque spring is arranged in the circumferential space between the ratchet tube and the reset tube and is at its proximal end secured to the spring base member 208 and at its distal end to the ratchet tube, whereby the spring is strained when the ratchet tube is rotated relative to the housing by rotation of the dial member. A ratchet mechanism with a flexible ratchet arm 252 is provided between the ratchet tube and the clutch element, the latter being provided with an inner circumferential teeth structures 242, each tooth providing a ratchet stop such that the ratchet tube is held in the position to which it is rotated by a user via the reset tube when a dose is set. In order to allow a set dose to be reduced a ratchet release mechanism 262 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
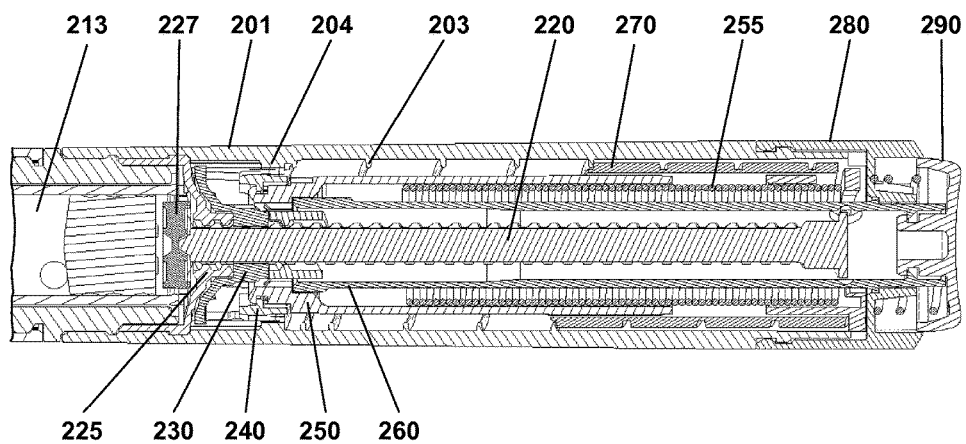

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 220, the actual displacement of the plunger being performed by the piston rod. During dose delivery, the piston rod is rotated by the drive element 230 and due to the threaded interaction with the nut element 225 which is fixed to the housing, the piston rod moves forward in the distal direction. Between the rubber piston and the piston rod, the piston washer 227 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 234 which prevent the drive element from rotating clockwise (seen from the push button end). Due to the engagement with the drive element, the piston rod can thus only move forwards. During dose delivery, the drive element rotates anti-clockwise and the ratchet arms 235 provide the user with small clicks due to the engagement with the ratchet teeth 205, e.g. one click per unit of insulin expelled.

Turning to the dial system, the dose is set and reset by turning the dial member 280. When turning the dial, the reset tube 260, the EOC member 228, the ratchet tube 250 and the scale drum 270 all turn with it. As the ratchet tube is connected to the distal end of the torque spring 255, the spring is loaded. During dose setting, the arm 252 of the ratchet performs a dial click for each unit dialed due to the interaction with the inner teeth structure 242 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 202.

The ratchet 252, 242 between the ratchet tube and the clutch element 240 prevents the spring from turning back the parts. During resetting, the reset tube moves the ratchet arm 252, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 242 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
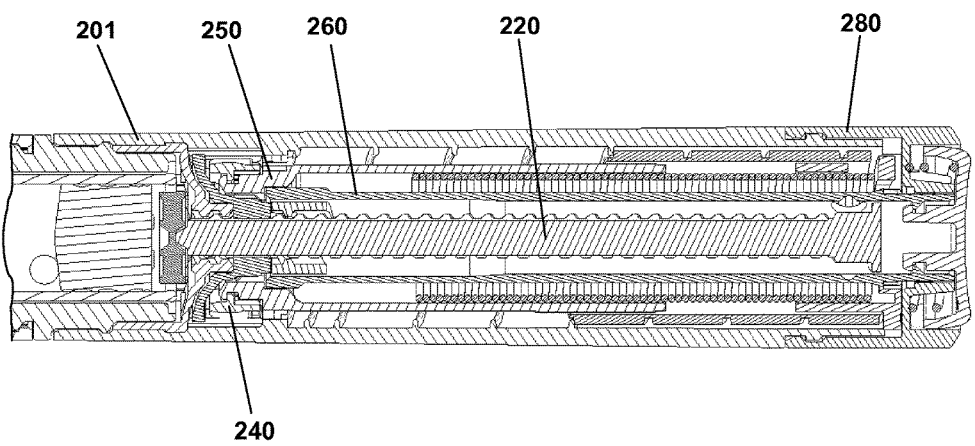

To deliver a set dose, the push button 290 is pushed in the distal direction by the user as shown in FIG. 3B. The reset tube 260 decouples from the dial member and subsequently the clutch element 240 disengages the housing splines 204. Now the dial mechanism returns to "zero" together with the drive element 230, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 228 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 270 is provided with a distal stop surface 274 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 206 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 281 engaging a number of corresponding teeth arranged on a flexible carrier portion 261 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism.

Thus, the mechanism inside the pen cannot be stressed at a higher load than the torque limiter transmits through the teeth.

Having described the working principles of a mechanical drug delivery device embodiments of the present invention will be described.

Figure 4:
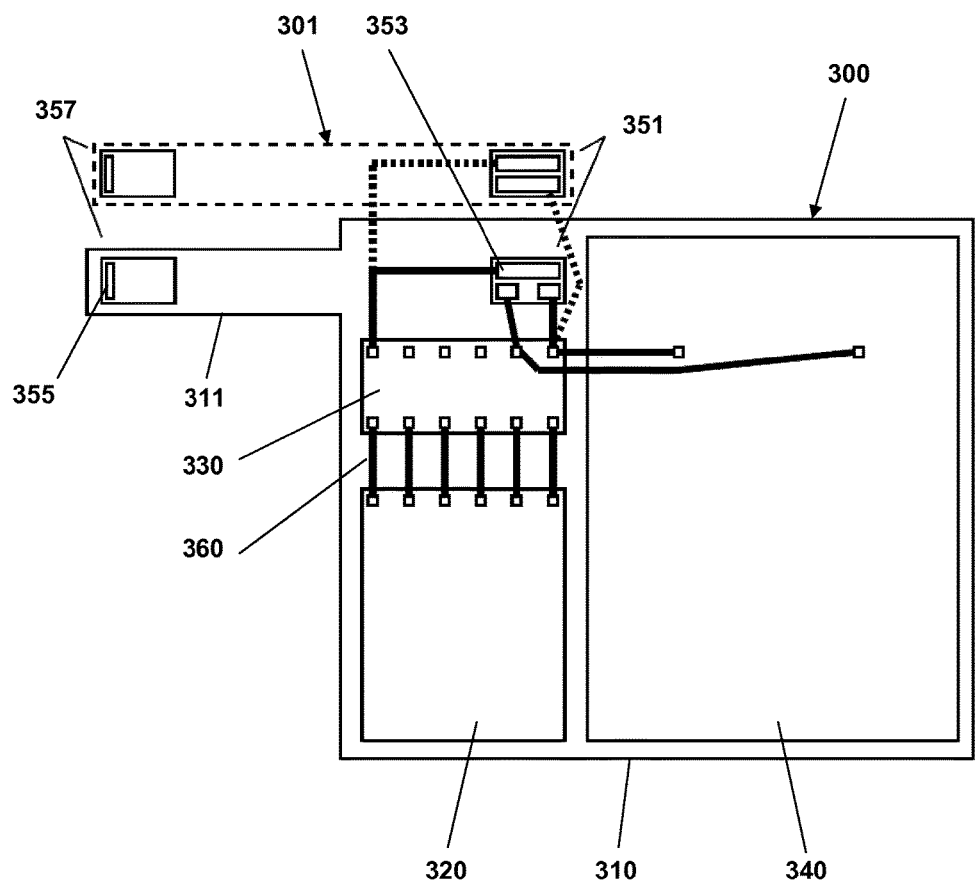
FIG. 4 shows a schematic representation of an "electronic label"
Figure 7:
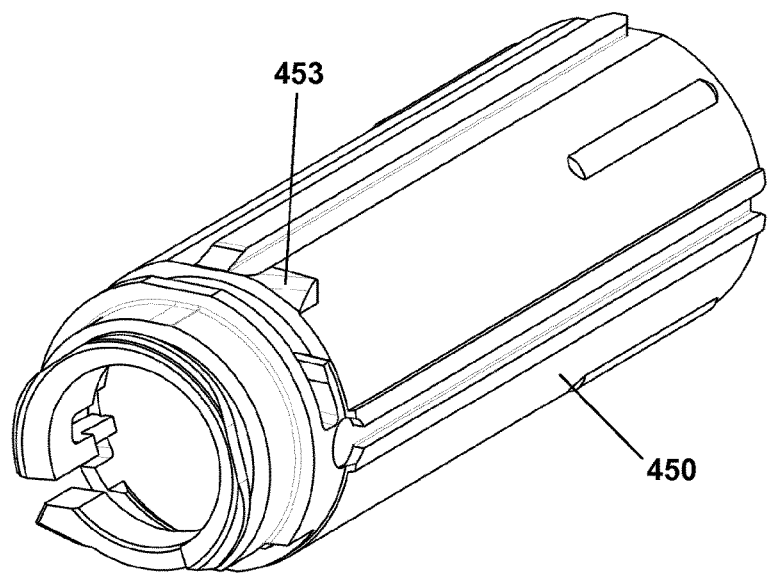
FIG. 7 shows a modified component of the expelling mechanism of FIG. 2.
Figure 8:
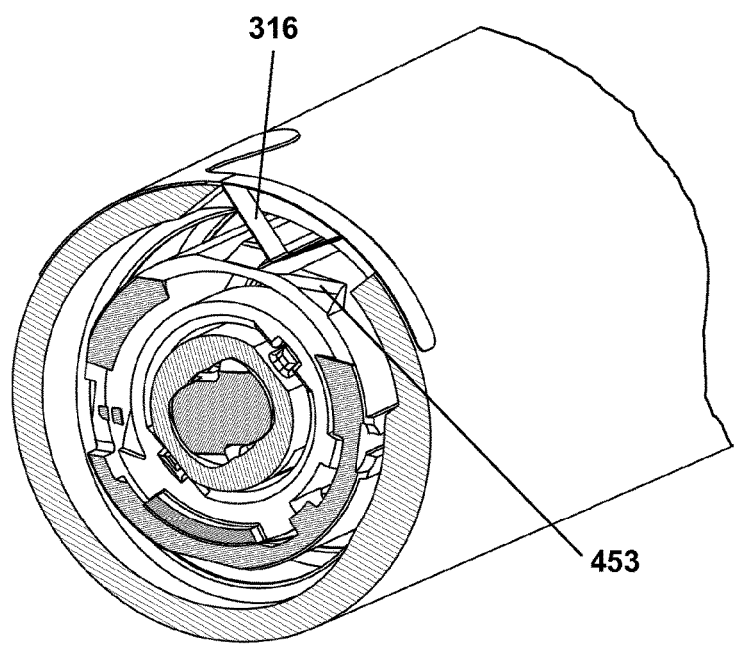
FIG. 8 shows in a cross-sectional view actuation of a switch mounted on the pen of FIG. 4, FIGS. 9A-9F show a time-indicating display for an "electronic label" in different states.

FIG. 4 shows a schematic representation of an "electronic label" 300 in the form of a flexible sheet on which a number of structures are mounted or formed. The shown exemplary embodiment and the specific switch arrangement is adapted to be used with a pen device as disclosed in FIGS. 5, 7 and 8 described below.

More specifically, the label is formed from a polymeric flexible sheet substrate 310 and comprises a printed display 320, either a printed logic unit or a mounted chip 330 (or a combination of the two), at least one battery 340 which is either printed onto the substrate, laminated or mounted to it, input means in the form of a first switch structure 350 which may be either a Single Pole Single Throw (SPST) switch or a Single Pole Double Throw (SPDT) switch, and a printed circuit comprising a plurality of individual leads 360 connecting terminals of the different components. A SPST switch is the simplest, while the SPDT can prevent drainage of the battery if necessary. In FIG. 4 the SPST switch is shown as an alternative configuration 301 in a dotted outline. An antenna (not shown) may also be formed on the flexible sheet by printing, the processor being adapted to transmit data to an external receiver via the antenna.

When the switch structure is activated a pulse is sent to the logic unit/chip which is then activated and starts a timer. The current stage in the timing cycle can be viewed on the display.

The timing cycle can consist of several sub-cycles, each of which may be related to a changed configuration of the display. If the switch is activated while the timer is running, the timer is reset and starts a new timing cycle.

The first switch structure consists of an area 351 with printed pads 353 (two for a SPST switch, three for a SPDT switch) adapted to cooperated with a second switch structure in the form of another area 357 with a conducting bar 355 serving to activate the label, the two switch structures forming a combined switch. When activated (see below) the conducting bar slides to connect the two pads of an SPST switch or from one position to the other for a SPDT switch. The area with printed pads is adapted to be mounted over an opening in a pen housing and the other area with the conducting bar is placed on a tongue 311 which is folded over and arranged in the opening thereby forming a mechanically actuated switch (see below). An indicator element in the pen interacts with the tongue to close (for the SPST switch) or change the connection (for the SPDT switch) during actuation.

Figure 5:
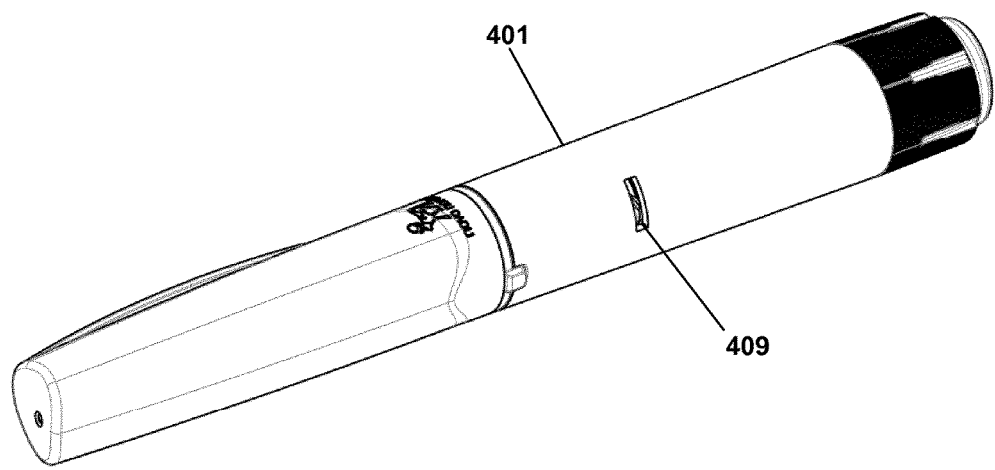
FIG. 5 shows a modified pen device to be used with an electronic label.

FIG. 5 shows a pen of the type shown in FIG. 1A but seen from the opposed "rear" side with the display window facing away. In contrast to the "base" pen described with reference to FIGS. 2 and 3 the pen of FIG. 5 has been adapted for application of an electronic label of the type shown in FIG. 4. More specifically, the housing 401 now comprises an opening 409 for a switch structure just as the ratchet tube 450 (see FIG. 7) serving as the indicator element has been provided with a protrusion 453.

Figure 6:
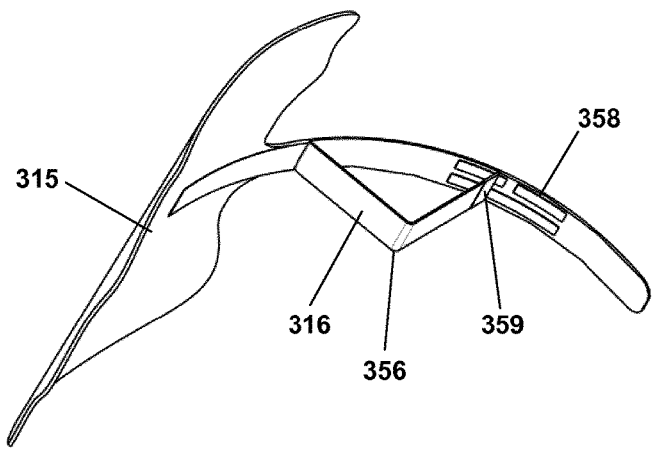
FIG. 6 shows an embodiment of a switch for an electronic label.

The switch shown in FIG. 6 corresponds to the combined switch structure described with reference to FIG. 4, however, instead of a folded unitary design the switch comprises a separate flexible strip portion 316 provided with a bend "knee" portion 356 and mounted on the flexible sheet 315 thereby forming the moveable switch portion. When the bended portion is compressed and subsequently released by an actuator structure the free contact end 359 shifts position back and forth on the stationary contact areas 358.

As described above the ratchet tube has a proximal position corresponding to a setting mode and a distal position corresponding to an expelling mode. In the embodiment of FIG. 5 the opening is arranged such that a mounted switch will be activated by the ratchet member protrusion only when it rotates in its expelling mode. As soon as the protrusion has passed the switch the switch returns to its idle position. In this way activation of the switch is coupled to the expelling of a dose of drug whereas the user can freely set and adjust a dose without activating the switch. As the ratchet tube protrusion for larger doses passes the switch a number of times the switch will correspondingly be activated a number of times for a single expelling event, however, as the actuations take place within a very short time this just means that the timer is reset a number of times, the last reset being the one from which the time-since-last-dose is counted. Alternatively, the first reset could be used with resets following within a short period being ignored.

Figure 9A:
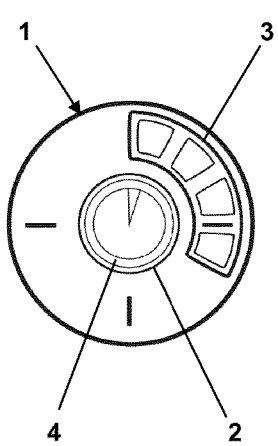
Figure 9B:
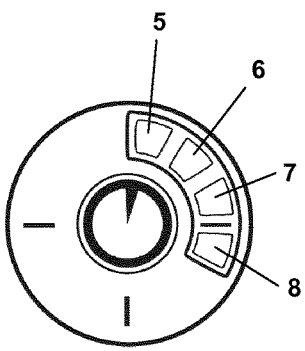
Figure 9C:
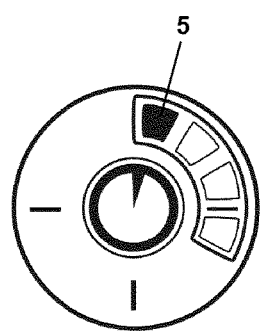
Figure 9D:
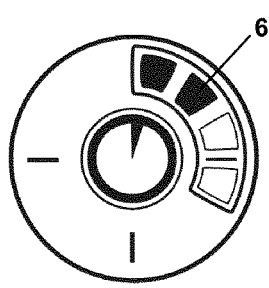
Figure 9E:
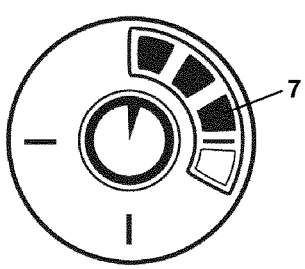
Figure 9F:
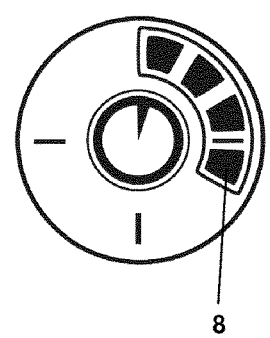

With reference to FIGS. 9A-9F a specific embodiment of a time-indicating display for an "electronic label" of the type shown in FIG. 4 will be described. The display 1 has a general circular configuration and comprises a central display area 2 and an outer curved display area 3 defined by printed borders. In the central display area an actuatable timer symbol 4 is formed using electronic ink and in the curved display area four actuatable counting segments 5, 6, 7, 8 are formed using electronic ink. In the shown embodiment the outlines of the individual actuatable segments are shown in the "off" state (FIG. 9A), however, this is mainly to indicate the presence of the structures in their non-actuated state. When the timer is turned "on" the timer symbol 4 is actuated from the inactive state (FIG. 9B), e.g. having the colour white, to the active state having the colour black. When a period of time has lapsed, e.g. one hour, the first 5 of the counting symbols is activated (FIG. 9C). Subsequently, for each additional hour a further counting segment 6, 7, 8 is actuated (FIGS. 9D and 9E) until all four counting segments are active (FIG. 9F), this indicating that at least four hours have lapsed since the time-indicating display was reset, i.e. actuated corresponding to a dosing event. In alternative embodiments more or less counting segments may be used just as the time period may be e.g. days instead of hours.

Figure 10A:
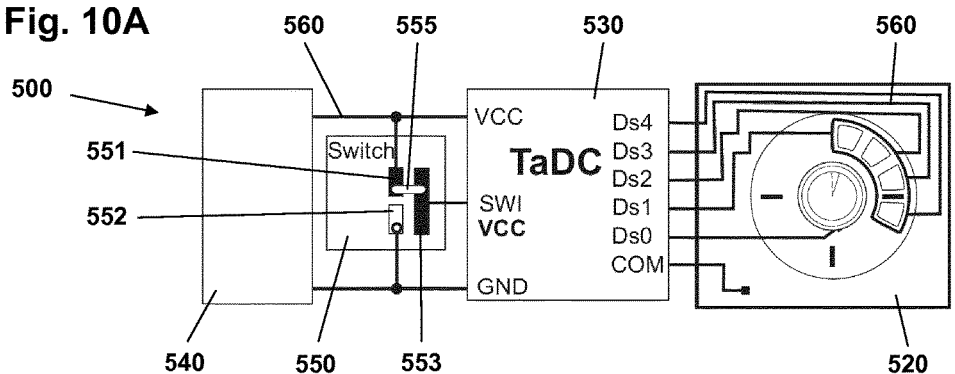
FIGS. 10A-10D show a schematic representation of an electronic label in different states.

Turning to FIG. 10A a schematic representation of an electronic label incorporating the time-indicating display 1 of FIG. 9A will be described. More specifically, the electronic timer label comprises a battery 540, a switch 550 (contact points only), a Timer and Display Controller chip ("TaDC") 530 and a display 520, all interconnected by printed electronic circuitry 560. The battery is connected to the TaDC and the switch, the switch on the label comprising two potential carriers 551, 552 connected to each of the battery poles and a potential carrier 553 connected to the switch input on the TaDC. In the shown embodiment the switcher is a separate mechanical part, however, it may be formed integrally with the label as described with reference to FIG. 4. The electronic label is made on a carrying foil by printing electronic circuits on the foil with conductive ink. The battery can either be printed or be a flexible battery attached and connected to the electronic circuitry or an external battery. The TaDC is a small dedicated chip attached and connected to the electronic circuitry. The display is printed on the label directly on the printed conductors for the display, each of the five display segments being connected to an individual output from the TaDC and to a common ground connection of the TaDC. A more detailed description of a manufacturing process for the label will be given below.

Figure 10B:
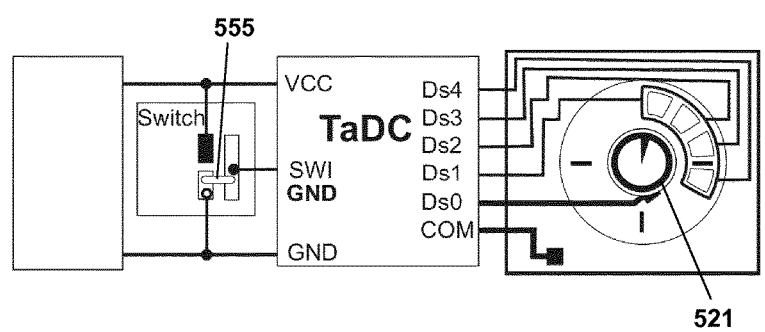
Figure 10C:
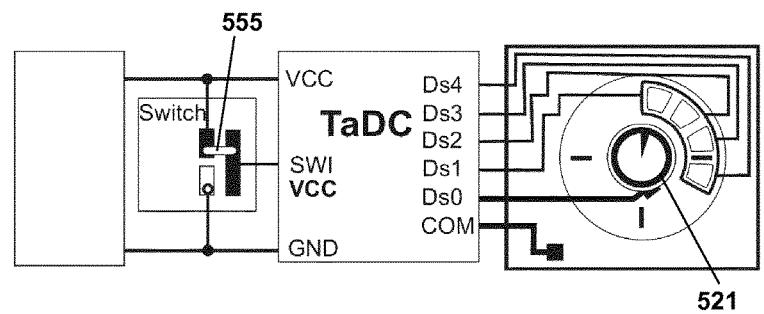
Figure 10D:
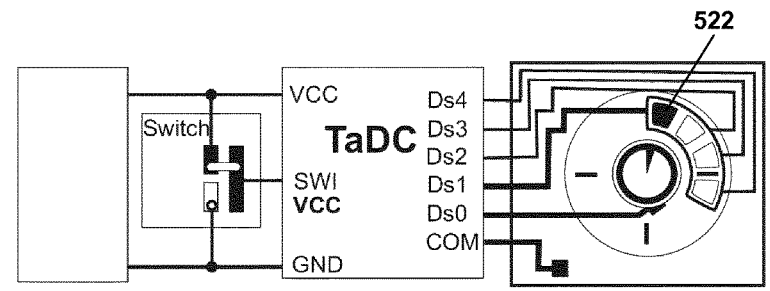

When the label is in an inactive state as shown in FIG. 10A the switcher 555 connects the potential carriers "VCC" 551 and "SWI" 553 and the SWI input on the TaDC is thus provided with a potential of VCC. None of the segments in the display are active in this state and the TaDC is in sleep mode with very low power consumption. When a dose is released by the device, the switcher slides over and connects the potential carriers "GND" 552 and SWI 553, which causes the SWI input on the TaDC to change from a potential of VCC to GND, this activating the system (FIG. 10B), the central timer symbol segment 521 now being turned on. The switcher shortly after returns to its original position, changing the potential on the SWI input of the TaDC back to VCC from GND (FIG. 10C). This however does not affect the now activated timer system, but enables the system to be restarted by changing the SWI input on the TaDC from VCC to GND again. When one hour has elapsed, the TaDC activates the first 522 of the four hour segments (FIG. 10D), while maintaining the active timer symbol segment in the active state. After each hour of elapsed time, an additional hour indicator segment is activated, until all five segments are activated when four hours have elapsed. After e.g. 5 hours the TaDC may power down to sleep mode. Depending on the type of e-ink used the segments may be left in their activated state or they may be deactivated together with the TaDC, the latter normally being the case if the segments require power to remain in the active state.

Figure 11:
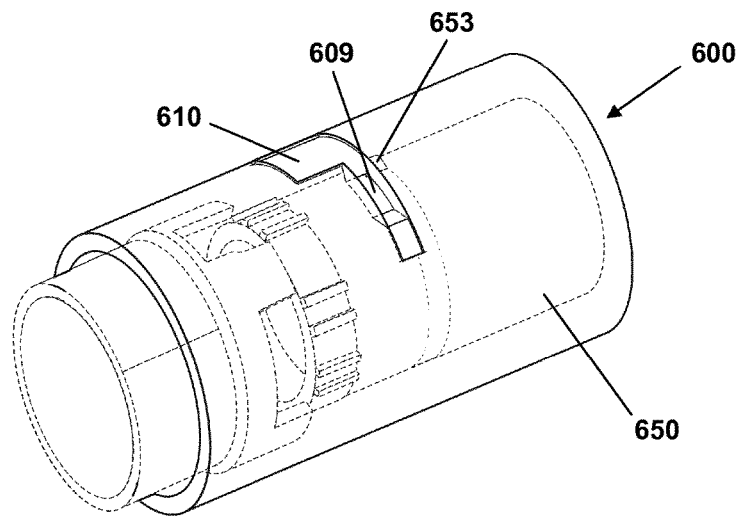
FIG. 11 shows in partial x-ray a portion of a drug delivery device adapted to be used with an electronic label.
Figure 12A:
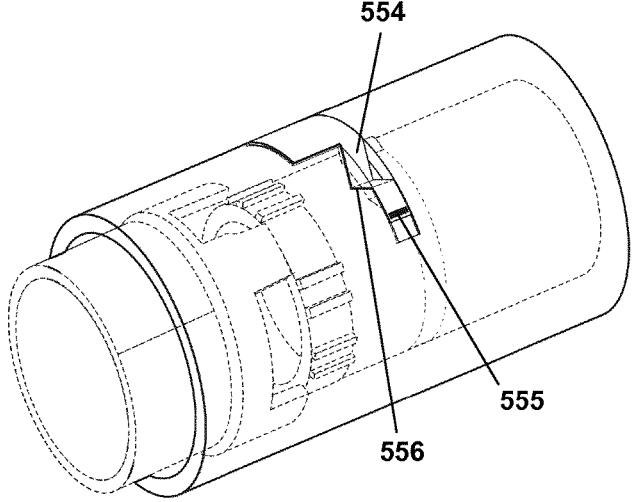
FIGS. 12A and 12B show the device of FIG. 11 with a mounted switch in two states.

With reference to FIGS. 11-13 the active part of the switch will be described. More specifically, FIG. 11 shows in partial x-ray a portion 601 of a drug delivery device (see FIG. 15.18) of the type described with reference to FIGS. 1-8, the device comprising an outer recessed area 610 with an opening 609, the recessed area allowing a bended flexible strip portion be mounted as shown in FIG. 12A in which a separate bended flexible strip portion 554 with an inwardly protruding "knee" 556 and a distal contact area 555 has been mounted. The device further comprises a ratchet tube 650 provided with a protrusion 653, this corresponding to the FIGS. 5-8 embodiment. An electronic label of the type described with reference to FIG. 4 is mounted on the device exterior surface providing that the strip portion with the contact area is retained in the recess.

Figure 12B:
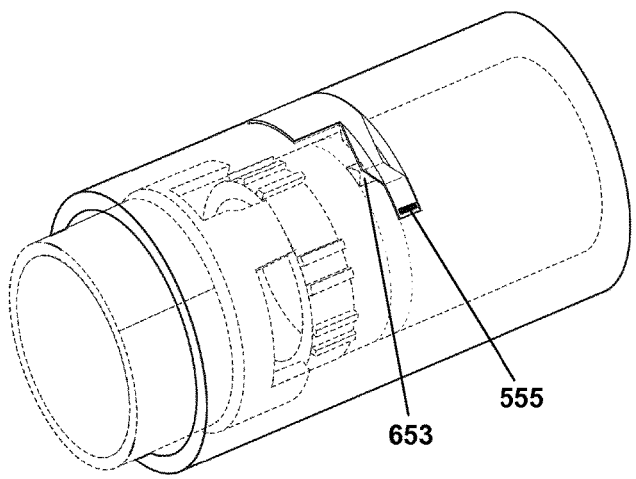

FIG. 12A shows the strip in its relaxed non-activated state with the contact area in a non-activated position, the ratchet tube being arranged in its proximal position. In FIG. 12B the contact strip has been activated by the scale drum protrusion and the contact area has been being moved to its activated position during the short period in which the protrusion passes the switch strip knee and forces it outwardly.

Figure 13A:
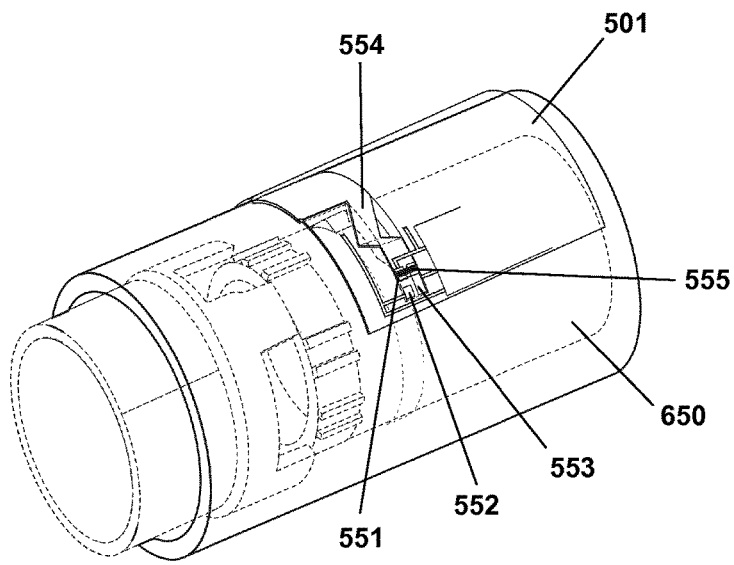
FIGS. 13A and 13B show the device of FIG. 11 with a mounted label in two states.
Figure 13B:
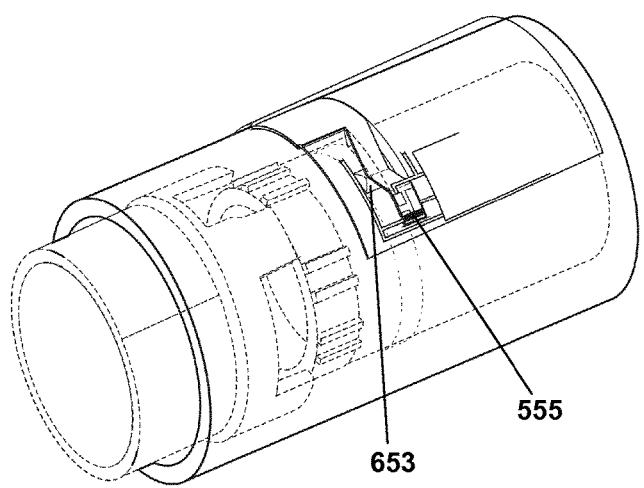

In FIG. 13A an electronic label 501 has been mounted with only the switch structures being shown, the switch state corresponding to the non-activated state described with reference to FIG. 10A. Correspondingly, FIG. 13B shows the switch state corresponding to the activated state described with reference to FIG. 10B.

Figure 14:
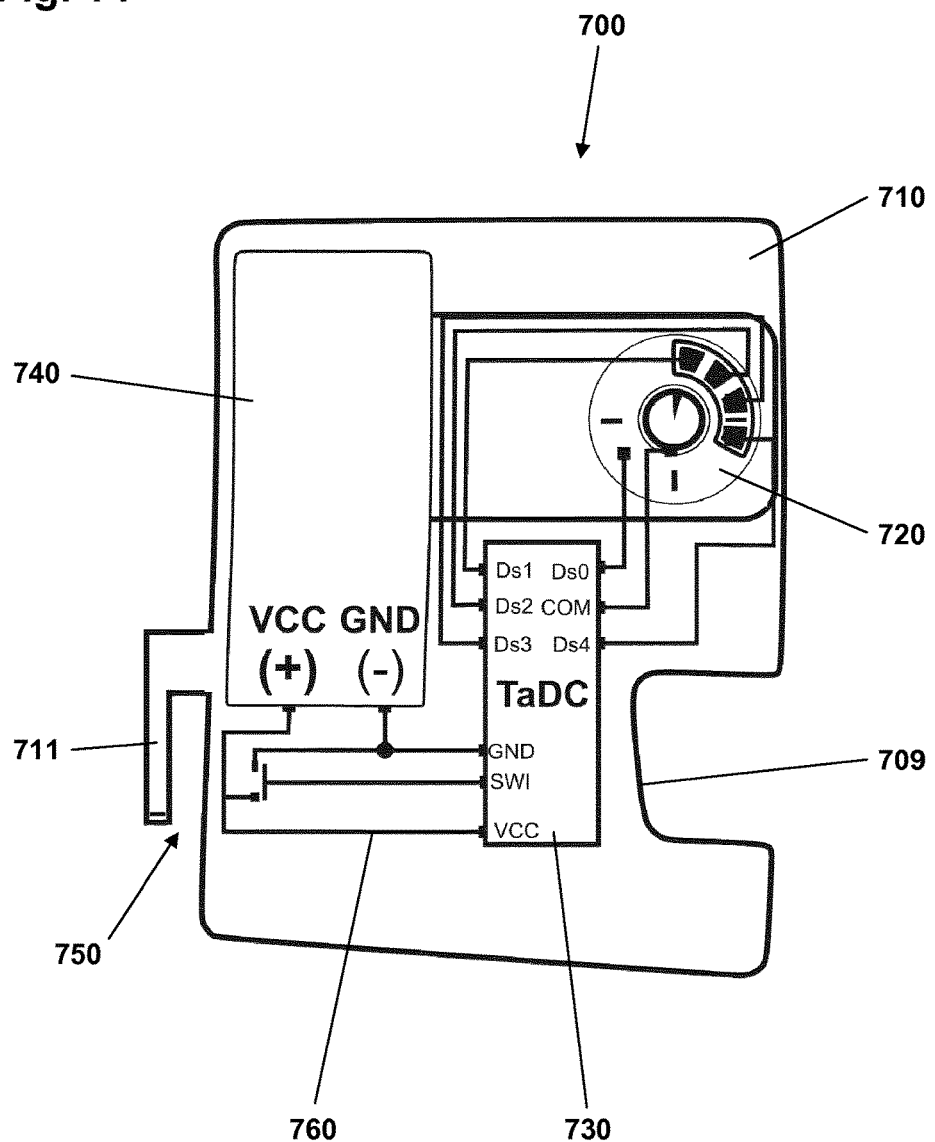
FIG. 14 shows an embodiment of an electronic label formed on a flexible foil, FIGS. 15.1-15.21 show different steps of a manufacturing process for an electronic label, FIGS. 16.1-16.7 show different states of use of a drug delivery pen with an electronic label.

FIG. 14 shows a further embodiment of an electronic label 700 formed on a flexible foil 710 and comprising a printed display 720, a mounted chip 730, a mounted battery 740, a switch 750 with a moveable strip part 711 formed integrally with the label, and a plurality of printed leads 760 connecting terminals of the different components. The label has a generally rectangular form with a cut-out 709 specific for the drug delivery device for which the label is intended. For illustrative purposes the TaDC is shown larger than the expected size for a commercial product.

Next, with reference to FIGS. 15.1-15.21, a manufacturing process for the electronic label 700 will be described. The different label structures are formed on a carrier substrate in the form of a continuous flexible foil strip which is moved step-wise through a line of manufacturing stations.

More specifically, FIG. 15.1 shows a portion of a transparent carrier foil strip 701 with the outline 702 of the label-to-be-formed indicated. In the first manufacturing step (FIG. 15.2) the label graphics 703 are printed on the lower surface of the foil and forms on the final product the outermost layer of the label. In the shown embodiment the print has an outline 704 corresponding to the final label (including the portion forming the future flexible strip portion 711) and carries for illustrative purposes a "Brand" and a "Drug" labelling 705. In the next step (FIG. 15.3) the display 720 is printed on the upper surface of the foil on a portion corresponding to a window formed in the label, this allowing the display to be viewed through the transparent foil. For illustrative purposes the label graphics are not shown. In the following step (FIG. 15.4) the circuitry leads 760 are printed providing the electric interconnections for the different terminals of the structures formed on or mounted on the foil. In the next step (FIGS. 15.5 and 15.6) a TaDC 730 and a flexible battery 740 are mounted on the foil upper surface. In the following step (FIG. 15.7) the switch contact areas are masked by a pair of masking members 801 and a protective layer 715 is applied on the remaining upper surface of the foil, the masking members serving to keep the contact areas 716 free of coating (FIG. 15.8). In the next step (FIG. 15.9) the switch contact areas surroundings are masked by a further masking member 802 and a layer of adhesive 717 is applied on the remaining upper surface of the foil, the masking members serving to keep the contact areas surroundings 718 and the flexible strip portion free from adhesive (FIG. 15.10). Thereafter a peelable protective sheet (not shown) is applied to the entire upper surface, this allowing the label to be handled and stacked after it has been cut out of the foil (FIG. 15.11), thereby producing a label 700 corresponding to the label shown in FIG. 14. Alternatively the foil may be wind onto a roll for later processing.

In the next steps, which may be performed just prior to mounting of the label on a drug delivery device, the free strip portion 711 is formed into its bend configuration using a pair of stamping tools 803 (FIGS. 15.12-15.15) after which the bend strip portion is folded over to form the final switch structure (FIGS. 15.16 and 15.17). Indeed, at this stage the protective sheet has been removed at least from the switch area. In the final steps the remaining protective sheet, if any, is removed and the flexible label 700 is attached to the outer curved surface 601 of a pen-formed drug delivery device 600 (FIGS. 15.18-15.21) to provide the finalized pen 605, the flexible strip portion 711 being arranged in a pen housing recess area 610, this providing a switch structure of the type described with reference to FIGS. 13A and 13B. In the shown embodiment the label display 720 is activated corresponding to a test mode in which all display segments are activated, this allowing defect labels to be identified prior to mounting.

With reference to FIGS. 16.1-16.7 use of the finalized pen product 605 of FIG. 15.21 will be described. The user receives the pen with the label in an inactive or sleeping state with all segments of the display in an "off" state, which would not change during setting of a dose by rotating the dose setting member 680 (FIG. 16.1). Thus, if the pen was reset to zero after a dose had been set and put away, the pen would remain in the inactive state. Correspondingly, if the release button 690 is actuated with no dose set the pen will remain inactive. When a dose has been set and the user releases the expelling mechanism to expel a dose, the ratchet tube 450 (FIG. 7) will be moved distally and start to rotate, this subsequently resulting in the label switch being actuated (FIG. 16.2) as described with reference to FIGS. 5-8, this turning on the central timer symbol 721. The pen label will remain in this state for an hour (FIG. 16.3) after which a counting symbol 722 will be activated (FIG. 16.4) with a further counting symbol 723, 724, 725 being activated for each subsequent hour as shown in FIGS. 16.5-16.7, i.e. after 2, 3 and 4 hours after delivery of a dose of drug. For the shown embodiment, after 5 hours all segments will be de-activated.

In the following a number of alternative switch arrangements for an electronic label of the above-described general type will be described.

Figure 17:
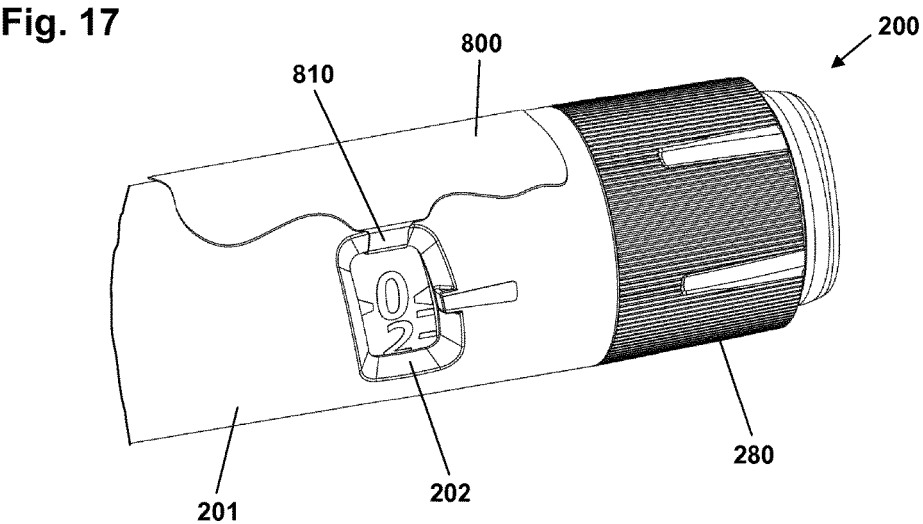
FIGS. 17 and 18 show an alternative for a switch design for a pen with external electronics.
Figure 18:
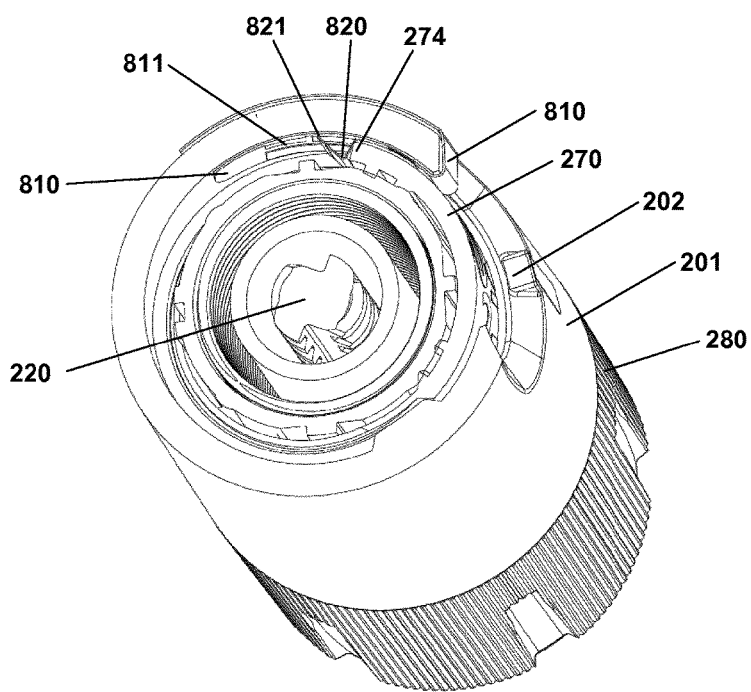

FIGS. 17 and 18 show in part an electronic label 800 mounted on a pen device 200 corresponding to the pen device described with reference to FIGS. 1-3 and thus comprising an unmodified housing 201. More specifically, the label comprises an integrally formed strip portion 810 arranged through the window opening 202 and mounted on the interior housing wall, the distal end portion of the strip comprising contact pads 811 corresponding to a SPDT contact as described above. Corresponding to the switch shown in FIG. 6 a flexible strip portion 820 with a "knee" portion and distal contact end 821 is mounted on the strip portion 810 thereby forming the moveable switch portion. The knee portion is arranged next to the scale drum distal stop surface 274 such that the switch is actuated to an on-state when a dose is set and returns to an off-state when the scale drum returns to the zero position, both events providing an input to the label circuitry.

In an alternative embodiment (not shown) the moveable switch portion may be provided on the indicator member, e.g. in the form of an electrically conducting projection arranged on the scale drum, the projection slidingly engaging the contact pads 811. To provide proper electrical contact one or both of the contact structure may be flexible allowing radial movement there between.

In a further alternative embodiment (not shown) the switch structure is in the form of a switch assembly comprising two flexible strip members, the assembly comprising a switch portion with a pair of opposed contact pads arranged on strip portions facing each other with a small distance, e.g. the strips may be mounted on a non-conducting supporting structure mounted on one or both side of the switch portion. The switch portion will typically be arranged on a distal part of the switch assembly adapted to be arranged in the interior of the pen, whereas a proximal part comprises mounting contact pads adapted to be connected with corresponding contact pads arranged on a subsequently mounted electronic label. Alternatively, the switch assembly may be formed fully or partly integrated with an electronic label. Corresponding to the switch arrangement of e.g. the FIG. 18 embodiment the flexible switch portion is arranged to be activated by an indicator member, e.g. the scale drum. Typically, also the "stationary" contact pad will be moved when the switch is actuated.

Figure 19:
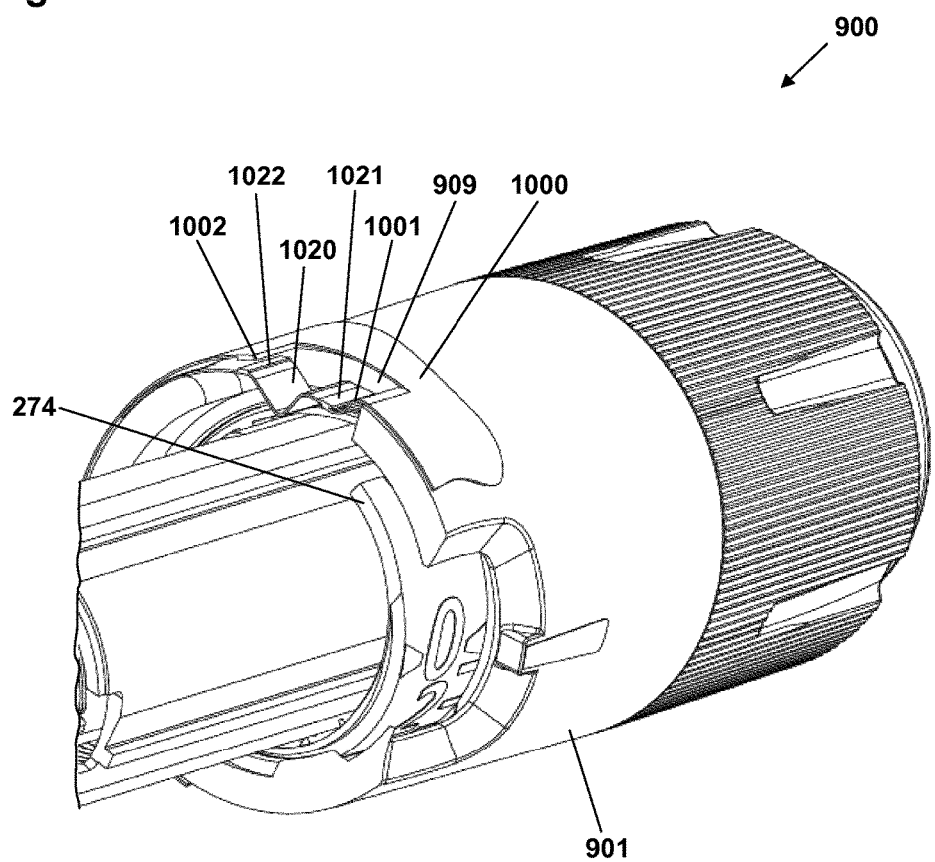
FIG. 19 shows a further alternative for a switch design for a pen with external electronics.

FIG. 19 shows in part an electronic label 1000 mounted on a pen device 900 corresponding to the pen device described with reference to FIGS. 1-3 but comprising a modified housing 901 in which an opening 909 is formed. Corresponding to the opening the label is provided with two contact pads 1001, 1002. A flexible strip 1020 with a "knee" portion and two contact pads 1021, 1022 and associated conductors is mounted on the label lower surface to thereby form a moveable switch portion providing a first switch comprising a first pair 1001, 1021 of contact pads and a second switch comprising a second pair of contact pads 1002, 1022. In the non-actuated state the first switch is in a closed state with the second switch in an open state. The knee portion is arranged next to the scale drum distal stop surface 274 such that the first switch is actuated to an off-state and the second switch to an on-state when a dose is set and returns to an on-respectively an off-state when the scale drum returns to the zero position, both events providing an input to the label circuitry. As appears, in contrast to the embodiment of FIG. 18 the contact pads generally do not slide relative to each other during actuation.

Figure 20:
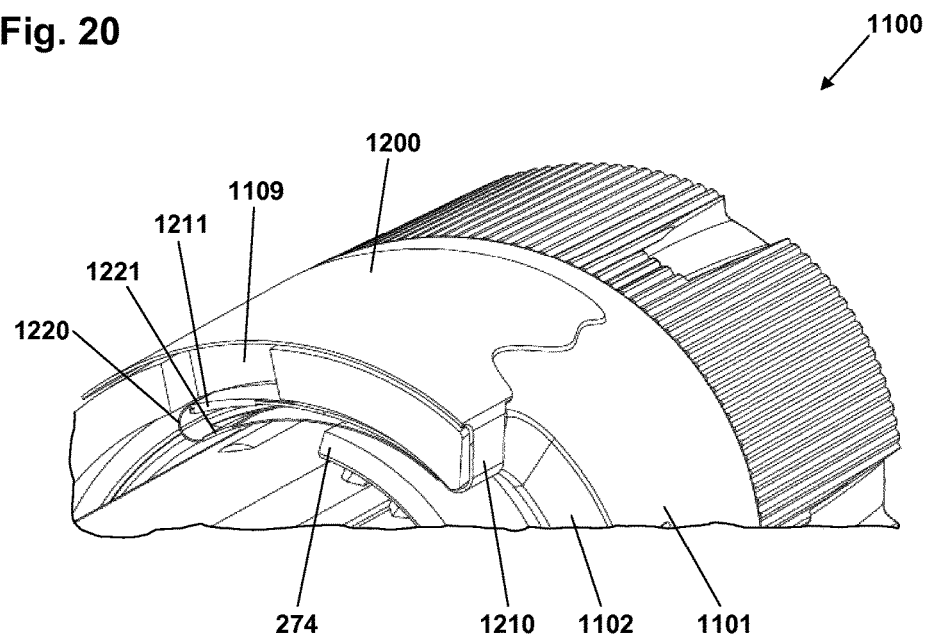
FIGS. 20 and 21 show a further alternative for a switch design for a pen with external electronics.
Figure 21:
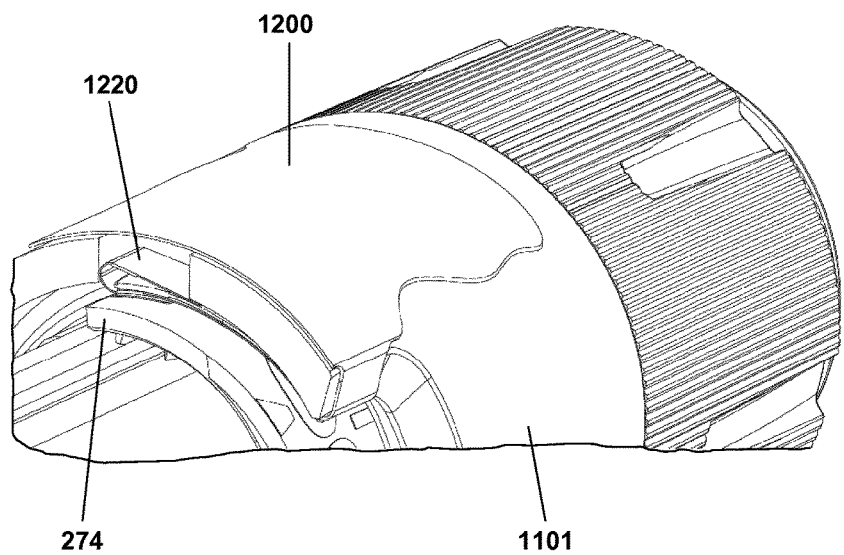

FIGS. 20 and 21 show in part an electronic label 1200 mounted on a pen device 1100 corresponding to the pen device described with reference to FIGS. 1-3 but comprising a modified housing 1101 in which an opening 1109 is formed. The label comprises an integrally formed strip portion 1210 arranged through the window opening 1102 and mounted on the interior housing wall, the distal end portion of the strip comprising a contact pad 1211 on each side. A flexible U-formed strip portion 1220 is mounted to the label strip in such a way that the distal U-portion can be moved up-down when the scale drum stop surface portion 274 is moved from and to the zero position as shown in the figures. Corresponding to the contact pads on the label strip the U-portion is provided with two contact pads 1021, 1222 and associated conductors thereby forming two switches. The U-portion is arranged next to the scale drum distal stop surface 274 such that the switches are operated between open and closed states corresponding to the FIG. 19 embodiment.

Figure 22:
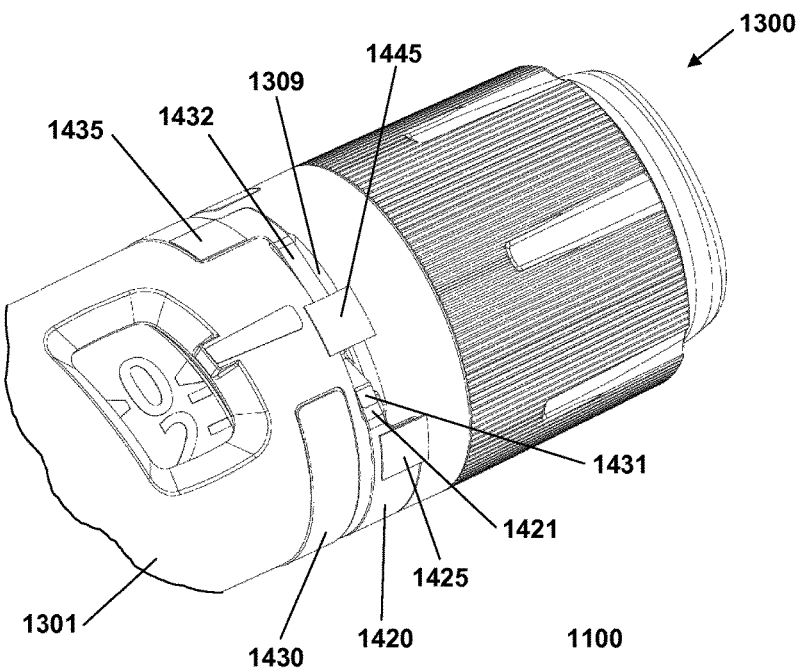
FIG. 22 shows a yet further alternative for a switch design for a pen with external electronics.

FIG. 22 shows in part a pen device 1300 corresponding to the pen device described with reference to FIGS. 1-3 but comprising a modified housing 1301 in which an opening 1309 is formed. First and second strip portions 1420, 1430 are mounted on the housing exterior surface; the first strip portion comprising a first contact pad 1421 mounted corresponding to a first end of the opening. The second strip portion comprises a flexible free knee portion arranged corresponding to the length of the opening, the free portion comprising an intermediate contact pad (see below) and a distal contact pad 1431 adapted to engage the first contact pad 1421. Three mounting pads (or terminals) 1425, 1435, 1445 are provided, a first pad 1425 being arranged on the first strip portion 1420 and connected to the first contact pad 1421, a second pad 1435 being arranged on the second strip portion 1430 and connected to the intermediate contact pad and the distal contact pad 1431, and a third pad mounted across the opening and being adapted to engage the intermediate contact pad. The first and second mounting pads may be formed integrally with the strip portions are applied as separate components. The mounting pads serve to create electric contact with corresponding contact pads (or terminals) arranged on a subsequently mounted electronic label. To activate the switch a protrusion provided on the scale drum engages the strip knee portion and thereby activates the switches as described above for the other switch designs.

Figure 23:
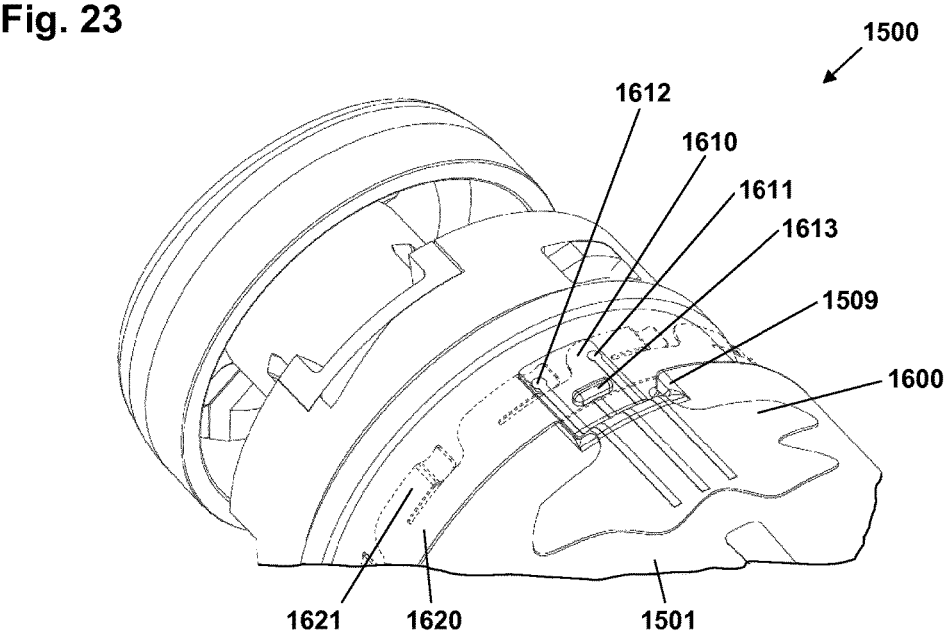
FIG. 23 shows a further alternative for a switch design for a pen with external electronics.

FIG. 23 shows in part an electronic label 1600 mounted on a pen device 1500 corresponding to the pen device described with reference to FIGS. 1-3 but comprising a modified housing 1501 in which a cut-out 1509 is formed. Corresponding to the cut-out the label is provided with a short strip 1610 comprising a contact protrusion 1613 and two contact pads 1611, 1612. On the lower interior circumferential surface of the rotatable dose setting member (not shown) a circumferential contact strip 1620 is mounted, the strip comprising a distal band portion (ground track) in constant sliding engagement with the contact protrusion 1613 and a plurality of proximal flexible contact fingers arranged to engage the label contact pads 1611, 1612 as the dose setting member is rotated relative to the pen housing. As appears, in this way a high number of contact events are created as a dose is set by a user. Depending on the actual design and location of the contact pads and contact fingers the switches may provide a rotary sensor and be used to detect the size of the dose being set.

Figure 24:
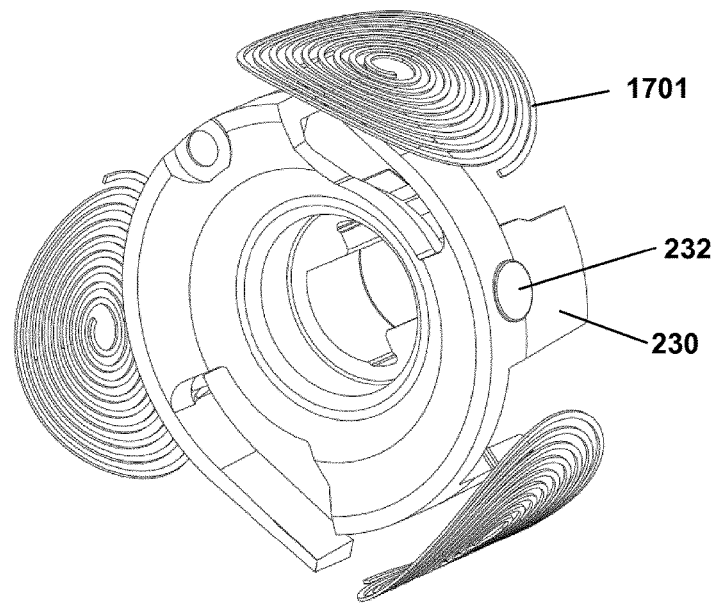
FIG. 24 shows an alternative for a sensor design for a pen with external electronics.

FIG. 24 shows a schematic representation of a switch arrangement based on magnetic induction, the drive element 230 being provided with one or more magnets 232 and the label being provided with a number, e.g. three, of printed induction coils 1710. The switch arrangement may be used for event, e.g. expelling of a dose, as well as dose size detection.

Figure 25:
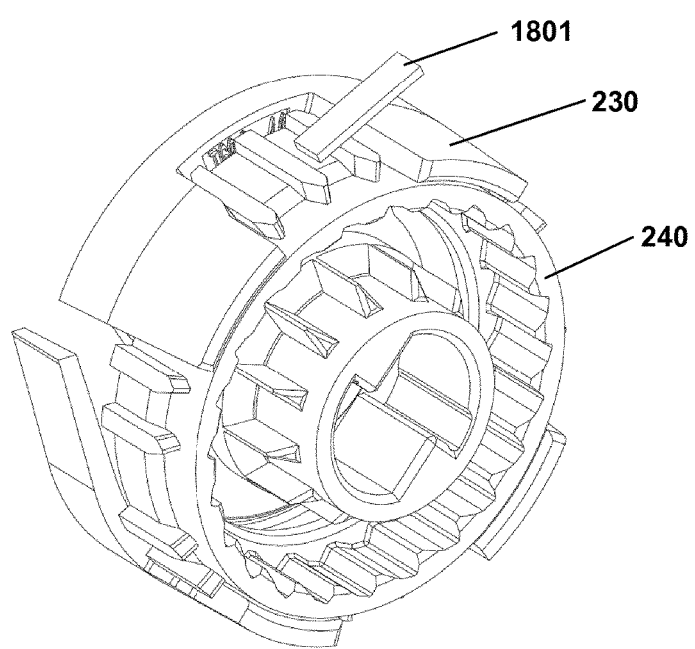
FIG. 25 shows a further alternative for a sensor design for a pen with external electronics.

FIG. 25 shows a schematic representation of a switch arrangement based on the label being provided with a piezo element 1801 being actuated during dose setting and/or dose expelling. The piezo element may be arranged on the exterior surface of the housing or it may be arranged to be actuated directly by an interior indicator element.

In a similar approach (not shown) the label may be provided with a strain gauge allowing deformations of the housing indicative of an expelling event to be detected, i.e. deformations caused by release of the energy stored in the drive spring. Alternatively an accelerometer may be incorporated in the label adapted to detect e.g. vibrations from the expelling mechanism during a dose setting or an expelling event.

FIG. 26 shows first and second contact members arranged to detect the size of a set and/or expelled dose. More specifically, the first contact member 1920 comprises an inner ring portion 1929 connected to three outer mounting contact pads 1925, 1926, 1927 via a strip portion 1928. The ring portion is adapted to be mounted on the proximally-facing surface of the nut element 225 (see FIG. 2) and comprises an inner circumferential ground track 1921 as well as outer and intermediate circumferential contact tracks 1922, 1923 each comprising a plurality of inwardly respectively outwardly oriented extensions. Each circumferential track is connected to a mounting pad and thereby to corresponding input contact pad on a subsequently mounted electronic label. The second contact member 1930 is in the form of a ring member adapted to be mounted on the distally facing surface of the drive element 230 via e.g. hook structures 1935. The ring member comprises a pair of flexible contact fingers 1931, 1932 adapted to engage the outer respectively intermediate track contact extensions in sliding on-off engagement as the ring member rotates with the drive element during expelling of a dose. The different structures are designed to provide a rotary sensor output allowing the size of an expelled dose to be detected by the electronic label circuitry, i.e. corresponding to arrangement of FIG. 23.

Figure 27:
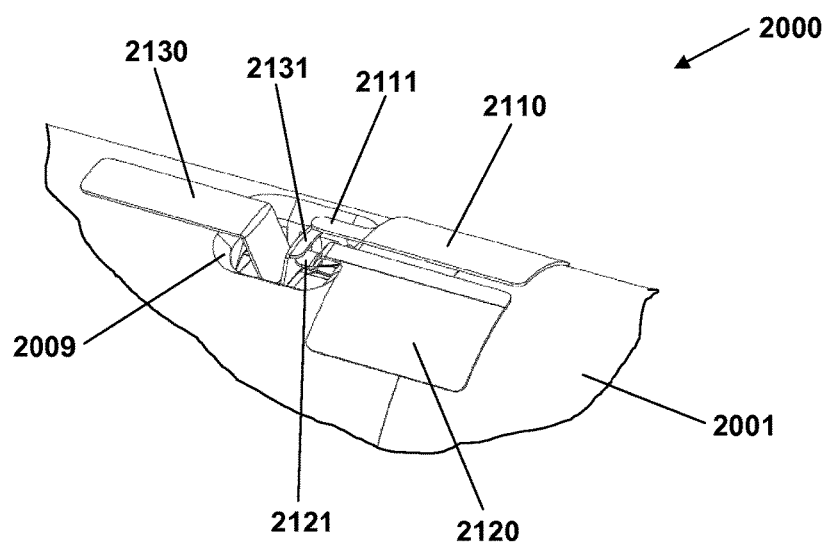
FIG. 27 shows a yet further alternative for a switch design for a pen with external electronics, FIG. 28.1 shows a further embodiment of a drug delivery pen with an electronic label, and FIGS. 28.2 and 28.3 show situations of use of the pen shown in FIG. 28.1.

FIG. 27 shows in part a pen device 2000 corresponding to the pen device described with reference to FIGS. 1-3 but comprising a modified housing 2001 in which an opening 2009 is formed. First, second and third strip members 2110, 2120, 2130 are mounted on the housing exterior surface. The first and second strip members comprise first and second stationary contact points 2111, 2121 connected to first and second mounting pads, and the third strip member comprises a flexible free knee portion arranged in the opening, the free end comprising a distal third contact point 2131 connected to a third mounting pad. The mounting pads serve to create electric contact with corresponding contact pads arranged on a subsequently mounted electronic label. To activate the switch a protrusion or edge portion provided on the ratchet tube 250 serves to actuate the switch when the ratchet tube is moved axially during dose release, the event providing an input to the label circuitry.

Corresponding to the above description of different switch designs, dose size sensing and dose event sensing switches may be combined, i.e. one set of switches may be used to detect a set and/or expelled dose size whereas an event switch may be used to detect that a set dose is actually expelled. Indeed, if dose size related information is to be displayed on the electronic label, corresponding numeric display means should be provided. In addition to a set dose and/or the size of the last set dose, also the remaining amount of drug in the cartridge could be displayed.

The above-described electronic label could be provided with additional features or the electronic label could be used as a platform to provide a drug delivery with further features. For example, manufacturers of insulin products often make different types of insulin, some of which are working rapidly but not for very long and others that works slower, but for longer time. As a further example a temperature sensor may be provided. The measured temperature may e.g. be used as an input for calculating a variable expiration date or warn against exposure to excessive temperatures. In addition to the above-described display features a logging functionality may be provided, e.g. a display graphically illustrating when drug was expelled, e.g. day and/or time. Warnings may be provided against e.g. double doses, maximum dose exceeded or other abnormal use. Personal settings may be entered wirelessly via e.g. an NFC antenna. The display means of the electronic label may be adapted to display 2D matrix codes which can be used to transfer data to e.g. a smartphone provided with a camera.

To keep manufacturing costs low, manufacturers often use the same type of device with as few as possible components (other than the insulin cartridge) differing. For prefilled devices the colour of the housing is usually the most distinctive (and often the only) visible difference between devices with different contents.

While mix-up of insulin types may be uncomfortable and inconvenient if slower working insulin is taken in a small dose instead of rapid working insulin, the opposite mix-up of taking a large dose of rapid working insulin instead of slower working insulin just prior of going to sleep may be fatal. Since the injections associated with the greater risk in case of mix-up is normally performed in the evening just prior to the user going to sleep, an increased risk of failure to notice if the wrong pen has been chosen exists, especially if the two devices have colours that may appear similar in sub-optimal light conditions.

Since users of a combination of both types of insulin are quite used to using both devices, even major differences in colour, shape, appearance and handling will not necessarily attract the users attention in case the user mix-up the devices, since the user uses both devices on a daily basis and get accustomed to both devices. This presents a risk that it would not feel awkward to use the wrong device/insulin type in a given situation. Worst scenario is a mix-up where a large dose of rapid working insulin is taken just prior to sleeping instead of slow working insulin. Such a mix-up could be fatal, but would not feel awkward since most users have used the rapid working insulin device 3-5 times earlier the same day. A $6^{th}$ time would not feel out of the ordinary.

The above problem is addressed by providing a flexible label of the same general design and construction as described above, the label containing a power supply, a processor, a user-actuatable switch and an area with controllable transparency. The label is marked to clearly indicate the contents and comprises two indicated button areas (though only one is actually a button). The label is designed to be mounted on a device of the type shown in FIG. 1A, i.e. comprising a window in which the set dose is shown, such that the area of controllable transparency covers the window of the device.

Besides clearly indicating the drug contents of the device, all labels have the same (at least two) buttons marked for different situations of use, related to the different available insulin types. The only operational button will be the button marked corresponding to the actual insulin type contained in the device, the other button(s) being "dummy" buttons. When the correct button is activated, the area of switchable transparency turns transparent for a limited time and allows the user to see the dose setting scale and adjust the dose size to be taken. Since no other buttons are active, the dose setting scale becomes visible only when user selects the correct type of insulin in the actual situation indicated by the user.

Correspondingly, by application of a label as described, the user would have to press the button symbolising the current situation. If user should forget to select the current situation (eating or sleeping), the dose setting scale will remain blinded, which prevents the user from setting the intended dose. If the user by mistake has taken the wrong device/insulin type and selects the current situation, the dose setting scale will be left blinded and the user is thus encouraged to investigate if correct device and situation has been selected and become aware of the mix-up prior to injection.

When user selects the current situation on the appropriate device, (the only really active button), the window of variable transparency becomes transparent and allows the user to dial a dose as intended.

FIG. 28.1 shows an embodiment of a pre-filled drug delivery pen 2200 comprising a drug cartridge 2210, an electronic label 2201 having been mounted, the label clearly indicating the type of drug 2011 contained in the device, in this case fast-acting NovoRapid® insulin provided by Novo Nordisk A/S, the label comprising a first operational button 2202 provided with a meal symbol, a second non-operative "dummy" button 2203 provided with a sleep symbol, a window 2204 with controllable transparency, and a dose setting button 2205.

When the user desires to use the device and thus set a dose to be expelled, the user has to activate the correct button, i.e. the button corresponding to the drug contained in the device. As the shown pen comprises fast-acting insulin the correct button is the one carrying the meal symbol. However, if the user actually desires to take a dose of long-acting insulin before going to bed, the user may grip the wrong pen overlooking that it contains fast-acting insulin, but when activating the sleep button as shown in FIG. 28.2 nothing happens and the window stays non-transparent, this providing a clear reminder to the user that the pen is not correct for the intended purpose. In contrast, if the user actually desires to take a dose of fast-acting insulin before taking a meal, the user activates the meal button 2203 as shown in FIG. 28.3 whereby the window becomes transparent allowing the user to view the scale drum numerals 2206.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device, comprising:
 a housing having an exterior surface,
 a drug-filled cartridge or structure for receiving a drug-filled cartridge, the drug-filled cartridge comprising an outlet and an axially displaceable piston,
 drug expelling structure comprising:
  a drive member adapted to engage and axially move the axially displaceable piston to thereby expel an amount of drug from the drug-filled cartridge through the outlet,
  an indicator member arranged to move corresponding to an action performed on or by the drug delivery device,
 a flexible sheet on which is formed or mounted:
  input structure adapted to be actuated, directly or indirectly, by movement of the indicator member,
  a display adapted to display a time parameter,
  a processor, and
  an energy source,
 wherein:
  the processor is adapted to, based on input from the input structure, control the display to display the time parameter related to a time of the input structure was actuated, and
  the flexible sheet is mounted at least in part to the exterior of the housing.

2. A drug delivery device as in claim 1, wherein the input structure is in the form of a switch structure adapted to be actuated between a first and a second state.

3. A drug delivery device as in claim 2, wherein the switch structure comprises a number of stationary contact areas formed or mounted on at least one contact area of the flexible sheet, the drug delivery device further comprising a moveable switch structure adapted to engage the at least one contact area to thereby actuate the input structure, the moveable switch structure being adapted to be moved by the indicator member.

4. A drug delivery device as in claim 3, wherein the moveable switch structure is formed integrally with the flexible sheet, the moveable switch structure comprising a contact area, wherein the contact area is arranged in its operational position by bending of the flexible sheet.

5. A drug delivery device as in claim 1, further comprising one or more switch members, wherein:
 the housing comprises an opening,
 the one or more switch members are arranged corresponding to the opening, at least one switch member is a moveable switch member projecting into the opening and being adapted to be moved by the indicator member, whereby the one or more switch members form a switch assembly adapted to be actuated between a first and a second state, and
 the flexible sheet is mounted to cover the opening, the flexible sheet comprising contact structure adapted to engage the switch assembly to thereby provide the input structure.

6. A drug delivery device as in claim 1, wherein:
 the indicator member is adapted to rotate from a set position corresponding to a set dose amount and to an end-of-dose position in which the set dose has been expelled,
 the input structure is actuated when the indicator member has reached the end-of-dose position, and
 the processor is adapted to control the display to display:
  a time parameter indicating the time when input structure was actuated, or
  a time parameter indicating the time since input structure was actuated.

7. A drug delivery device as in claim 6, wherein the indicator member has a first axial position when the drug expelling structure is in a dose setting state, and a second axial position when the drug expelling structure is in an expelling state, the input structure being adapted to be actuated by the indicator member with the indicator member only in the second axial position.

8. A drug delivery device as in claim 1, wherein:
 the indicator member is adapted to move from an initial position to a set position when a dose is being set,
 the input structure is actuated when the indicator member is moved away from the initial position, and
 the processor is adapted to control the display to display:
  a time parameter indicating the time when input structure was actuated, or
  a time parameter indicating the time since input structure was actuated.

9. A drug delivery device as in claim 1, wherein:
 an indicator member is adapted to move corresponding to a set and/or expelled amount of drug,
 the input structure and the processor are adapted to detect the set and/or expelled amount of drug, and
 the display is adapted to display a value corresponding to an amount of drug.

10. A drug delivery device as in claim 1, wherein:
 the housing has a curved exterior surface portion, and
 the flexible sheet and the display are mounted at least in part on the curved exterior surface portion of the housing.

11. A drug delivery device as in claim 1, wherein one or more or all of the input structure, display, processor, and energy source is/are in the form of printed electronics.

12. A drug delivery device as in claim 1, wherein an antenna is formed on the flexible sheet by printing, the processor being adapted to transmit or receive data to/from an external receiver via the antenna.

13. A drug delivery device as in claim 1, comprising:
 a drug-filled cartridge comprising a first type of drug,
 a first visual indicator indicating the first type of drug,
 a first user input structure associated with a second visual indicator indicating the first type of drug,
 a second user input structure associated with a third visual indicator indicating a second type of drug, and
 blocking structure having a first state preventing normal operation of the drug expelling structure, and a second state allowing normal operation of the drug expelling structure,
wherein:
 actuation of the first user input structure brings the blocking structure from the first state to the second state, thereby allowing normal operation of the drug expelling structure, and actuation of the second user input structure does not bring the blocking structure from the first state to the second state, thereby preventing normal operation of the drug expelling structure.

14. A drug delivery device, comprising:
a housing having an exterior surface,
a drug-filled cartridge or structure for receiving a drug-filled cartridge, the cartridge comprising an outlet and an axially displaceable piston,
a drug expelling structure comprising:
   a drive member adapted to engage and axially move the piston to thereby expel an amount of drug from the cartridge through the outlet,
   an indicator member arranged to move corresponding to an action performed on or by the drug delivery device,
   a flexible sheet on which is formed or mounted:
   input structure adapted to be actuated, directly or indirectly, by movement of the indicator member,
   an antenna,
   a processor, and
   an energy source,
wherein:
the processor is adapted to, based on input from the input structure, transmit or receive data to/from an external receiver via the antenna related to a time the input structure was actuated, and the flexible sheet is mounted at least in part to the exterior of the housing.

* * * * *